(12) United States Patent
Palli et al.

(10) Patent No.: US 11,571,394 B2
(45) Date of Patent: Feb. 7, 2023

(54) MODIFIED-RNA NANOPARTICLES FOR INDUCTION OF RNA INTERFERENCE

(71) Applicant: University of Kentucky Research Foundation, Lexington, KY (US)

(72) Inventors: Subba Reddy Palli, Lexington, KY (US); Ramesh Kumar Dhandapani, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 146 days.

(21) Appl. No.: 16/851,986

(22) Filed: Apr. 17, 2020

(65) Prior Publication Data

US 2020/0330395 A1 Oct. 22, 2020

Related U.S. Application Data

(60) Provisional application No. 62/835,351, filed on Apr. 17, 2019.

(51) Int. Cl.
*A61K 9/51* (2006.01)
*A61K 31/713* (2006.01)

(52) U.S. Cl.
CPC .......... *A61K 9/5146* (2013.01); *A61K 9/5115* (2013.01); *A61K 9/5123* (2013.01); *A61K 31/713* (2013.01)

(58) Field of Classification Search
CPC .. A61K 9/5146; A61K 9/5115; A61K 9/5123; A61K 31/713
See application file for complete search history.

(56) References Cited

U.S. PATENT DOCUMENTS 7,919,072 B1 * 4/2011 Sung .................. A61K 31/13
424/1.73

OTHER PUBLICATIONS

Hellman et al., PLoS ONE 5(1):e8682 (2010) (Year: 2010).*
Das, et al., Chitosan, Carbon Quantum Dot, and Silica Nanoparticle Mediated dsRNA Delivery for Gene Silencing in Aedes aegypti: A Comparative Analysis, ACS Appl. Mater. Interfaces 2015, 7, 19530-19535.
Kumar, et al., Delivery of chitosan/dsRNA nanoparticles for silencing of wingdevelopment vestigial (vg) gene in *Aedes aegypti* mosquitoes, International Journal of Biological Macromolecules 86 (2016) 89-95.
Mysore, et al., Disruption of Aedes aegypti Olfactory System Development through Chitosan/siRNA Nanoparticle Targeting of semaphorin-1a, PLOS Neglected Tropical Diseases, May 2013, vol. 7, Issue 5, e2215, pp. 1-12.
Zhu, K.Y. and S.R. Palli, Mechanisms, Applications, and Challenges of Insect RNA Interference. Annu Rev Entomol, 2020. 65: p. 293-311.
Palli, S.R., RNA interference in Colorado potato beetle: steps toward development of dsRNA as a commercial insecticide. Current Opinion in Insect Science 2014, 6:1-8.
Dhandapani, R.K., et al., Development of CS-TPP-dsRNA nanoparticles to enhance RNAi efficiency in the yellow fever mosquito, *Aedes aegypti*. Sci Rep, 2019. 9(1): p. 8775.
Zhang, X., J. Zhang, and K. Y. Zhu. "Chitosan/double-stranded RNA nanoparticle-mediated RNA interference to silence chitin synthase genes through larval feeding in the African malaria mosquito (*Anopheles gambiae*)." Insect molecular biology 19.5 (2010): 683-693.
Zhu, F., Xu, J., Palli, R., Ferguson, J. & Palli, S.R. Ingested RNA interference for managing the populations of the Colorado potato beetle, *Leptinotarsa decemlineata*. Pest Manag Sci. 67(2), 175-182. doi: 10.1002/ps.2048 (2011).

* cited by examiner

*Primary Examiner* — Robert S Cabral
(74) *Attorney, Agent, or Firm* — Stites & Harbison PLLC; Mandy Wilson Decker

(57) ABSTRACT

Improved RNA interference (RNAi) efficiency in insects is disclosed herein. In particular, certain embodiments of the presently-disclosed subject matter relate to use of nanoformulations of double-stranded RNA (dsRNA) to limit nuclease degradation of the dsRNA, and enhance cellular update and intracellular transport to improve delivery of the dsRNA to enhance RNAi in insects.

16 Claims, 27 Drawing Sheets

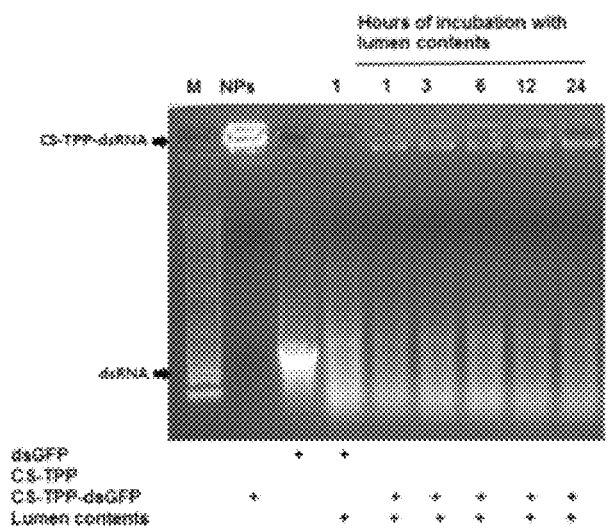
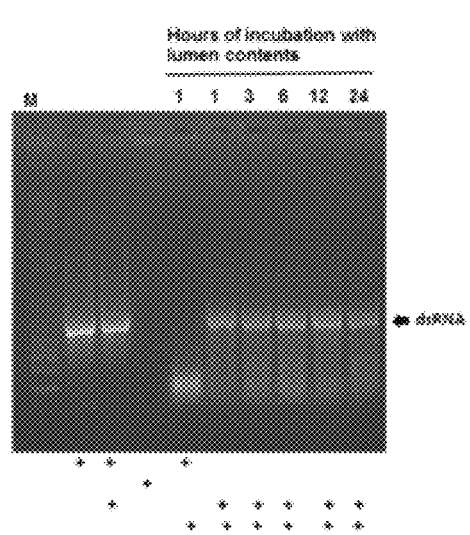
FIG. 2A  FIG. 2B
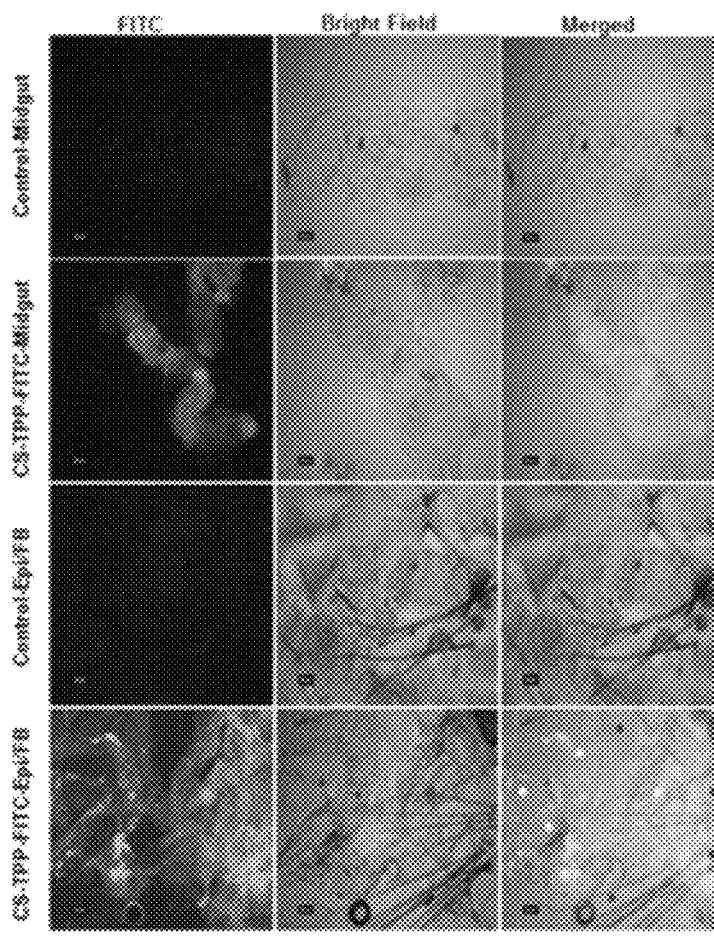
FIG. 3

1 kb ladder
PLL-dsRNA
PLL-EGCG-dsRNA

1kb ladder
dsRNA
Medium
PLL:dsRNA
PLL:EGCG:dsRNA
Serum-media
Conditioned-medium 1 kb ladder
dsRNA
PS:Cf:dsRNA (1:0.1:1)
PS:Cf:dsRNA (3:0.1:1)
PS:Cf:dsRNA (5:0.1:1)
PS:Cf:dsRNA (10:0.1:1)

Figure 2 Different ratio of PS:Cf:dsRNA nanoparticles testing the luciferase activity in Sf9 cells expressing the luciferase gene. The results showed that 78.4% reduced expression of the luciferase gene in the ratio of PS:Cf:dsRNA (10:0.1:1); Asterisk show statistical difference (P<0.05).

MODIFIED-RNA NANOPARTICLES FOR INDUCTION OF RNA INTERFERENCE

RELATED APPLICATIONS

This application claims priority from U.S. Provisional Application Ser. No. 62/835,351 filed Apr. 17, 2019, the entire disclosure of which is incorporated herein by this reference.

GOVERNMENT INTEREST

This invention was made with government support under Grant Nos. NH 3200001140, GM070559-12 and 1R21AI131427-01 and National Institute of Food and Agriculture, US Department of Agriculture (under HATCH Project 2351177000). The government has certain rights in the invention.

TECHNICAL FIELD

The presently-disclosed subject matter generally relates to improving RNA interference (RNAi) efficiency in insects. In particular, certain embodiments of the presently-disclosed subject matter relate to use of nanoformulations of double-stranded RNA (dsRNA) to limit nuclease degradation of the dsRNA, and enhance cellular update and intracellular transport to improve delivery of the dsRNA to enhance RNAi in insects.

INTRODUCTION

There are a number insects that cause significant issues. For example, the Asian longhorn beetle (Coleopteran) is a notable forest pest and the fall armyworm (Lepidopteran), a worldwide invasive pest. Furthermore, various viral diseases are vectored by the yellow fever mosquito, Aedes aegypti. These vector-borne diseases include chikungunya, yellow fever, dengue and zika affect millions of people around the world [1]. These disease vectors are broadly distributed and capable of developing from egg to adult in as little as 7-10 days. Vector control is an essential strategy to reduce transmission and prevent the occurrence of vector-borne diseases.

Conventional methods for insect control include repellents, insecticidal sprays, and insecticide-treated nets. For example, in connection with mosquitoes, management of larvae is typically limited to insecticidal treatments and removal of standing water sources in areas where mosquito populations are abundant. However, the efficacy of these methods has been decreasing over time due to widespread development of resistance to insecticides and growing environmental concerns of residual toxicity [2].

RNA interference (RNAi) is a sequence-specific, post-transcriptional gene silencing method, which can be triggered by the introduction of double-stranded RNA (dsRNA), and could be useful in this context [3]. RNAi mediated gene silencing has been demonstrated as an important alternative to chemical insecticides in controlling pests such as the western corn rootworm [6]. An RNAi-based product to control western corn rootworm has recently been approved by US EPA. A few other products to control coleopteran pests such as Colorado potato beetle and flea beetle are under development.

Although RNAi is a highly conserved mechanism in eukaryotes including fungi, plants, insects, and mammals [4,5,6,7,8,9] there are still hurdles for successful implementation of RNAi to knockdown genes in many species of insects [10]. RNAi varies among insects; highly efficient and systemic in coleopteran insects but variable and inefficient in most other insects [61]. The variable RNA efficiency among insects is one of the major hurdles preventing the widespread application of RNAi technology for pest and vector control [61].

Lack of suitable delivery methods for dsRNA and variability in cellular uptake and transport of dsRNA in insects are significant challenges in gene silencing efforts. Additionally, dsRNA must overcome specific obstacles such as poor cellular internalization, rapid degradation by nucleases, and limited blood stability [11]. Another limitation for successful RNAi in insects is the lack of conserved dsRNA transporter genes, resulting in a poor systemic RNAi response [12]. Also, dsRNA is prone to degradation by nucleases in the body of the insect [13].

Indeed, recent studies revealed that dsRNA degradation by nucleases present in lumen and hemocoel, it's poor transport into and within cells, endosomal accumulation and absence of critical players in RNAi pathway contribute to variable RNAi efficiency [62-68].

Nanoparticle-mediated gene delivery systems are being developed to overcome some of these limitations and deliver dsRNA to site of action within the cell efficiently. To date, a variety of nanoparticles have been designed for delivery of dsRNA [69-74]. Among them, polymeric nanocarriers are effective delivery of dsRNA for both in vitro and in vivo. Cationic polymers and nucleic acids form nanoparticles through electrostatic interaction [75-77]. These interactions are weak and therefore could be easily disassociated under alkaline pH conditions in the lumen of most insects [54, 78, 79].

Increasing the intermolecular interaction strength in nanoparticles by using high molecular weight polymers could affect the stability of nanoparticles under different pH conditions and enhance toxicity [79, 80]. As a result, low molecular weight polymers and nucleic acids were being assembled into biocompatible nanoparticles for delivery of dsRNA [81, 82, 86]. However, the methods developed so far for delivery of dsRNA improved RNAi efficiency in some insect species but not to the level required for commercial application of this technology [61].

Accordingly, there is a need in the art for improved compositions and methods for improved RNA interference (RNAi) efficiency in insects.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes compositions and methods for improving RNA interference (RNAi) efficiency in insects. In particular, certain embodiments of the presently-disclosed subject matter relate to use of nanoformulations of double-stranded RNA (dsRNA) to limit nuclease degradation of the dsRNA, and enhance cellular update and intracellular transport to improve delivery of the dsRNA to enhance RNAi in insects.

In some embodiments, the composition includes a double stranded RNA (dsRNA) molecule for initiating RNA interference (RNAi) in an insect, and a delivery-enhancing agent, assembled with the dsRNA in a nanoparticle.

In some embodiments, the delivery-enhancing agent includes (-) epigallocatechin-3-O-gallate (EGCG). In some embodiments, the delivery-enhancing agent also includes a polymer.

In some embodiments, the polymer is a polyamino acid. In some embodiments, the polymer is selected from the group consisting of: polylysine, polyargenine, polyhistodine and other polyamino acids. In some embodiments, the ratio of polymer to EGCG is from about 1:10 to about 10:1. In some embodiments, the ratio of polymer to EGCG is about 1:3.

In some embodiments, the delivery-enhancing agent includes Chitosan (CS) and a cross-linker as components of the delivery enhancing agent. In some embodiments, the cross-linker is sodium tripolyphosphate, dextran sulfate, or poly-D-glutamic acid. In some embodiments, the ratio of CS to cross-linker is from about 4:1 to about 6:1.

In some embodiments, the delivery-enhancing agent includes protamine sulfate (PS) as a component of the delivery enhancing agent. In some embodiments, the delivery-enhancing agent also includes a cationic-lipid formulation for transfecting insect cells. In some embodiments, the cationic-lipid formulation is CELLFECTIN® or CELLFECTIN® II.

In some embodiments, the nanoparticle of the composition has a mean size equal to or less than about 200 nm.

In some embodiments, the dsRNA of the composition encodes a polypeptide, or a fragment thereof, selected from the group consisting of inhibitor of apoptosis (IAP), vacuolar-sorting protein SNF7 (SNF7), snakeskin (SSK), and off-track (OTK), and combinations thereof.

The presently-disclosed subject matter further includes a method of inducing RNAi in a cell, comprising: contacting the cell with the composition as disclosed herein. In some embodiments, the cell is in an insect. In some embodiments, the insect is a mosquito. In some embodiments, the insect is an Asian longhorn beetle. In some embodiments, the insect is a fall armyworm.

In some embodiments, the method includes contacting the cell with the composition suppresses expression of one or more genes selected from the group consisting of dsIAP, dsSNF7, dsSSK, dsOTK, and combinations thereof.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 1A: The formation of CS-TPP-dsRNA complexes was verified by agarose gel electrophoresis. 1 Kb ladder, naked dsRNA and CS-TPP-dsRNA complexes were resolved on 1% (w/v) agarose gel, stained with GelRed® and photographed under UV light. The picture of gel shows differences in the migration of free dsRNA and CS-TPP-dsRNA complexes. FIGS. 1B and 1C: The mean particle diameter (z-average), polydispersity (PDI), and zeta potential (surface charge) of freshly prepared CS-TPP-dsRNA nanoparticles were determined by photon correlation spectroscopy (PCS) using Zetasizer (Malvern Instruments, UK). All measurements were performed in triplicate at 25° C. and data are reported as mean±standard deviation. FIGS. 1D and 1E: Morphological characterization of CS-TPP-dsRNA nanoparticles was carried by Transmission electron microscopy. A drop of CS-TPP-dsRNA nanoparticles on the copper microgrid was natively stained with 2% phosphotungstic acid and photographed under a TEM (HRTEM, JEOL 2010F, Japan.

FIGS. 2A and 2B shows the stability of CS-TPP-dsRNA nanoparticle complexes exposed to lumen contents of mosquito larvae was assessed by gel electrophoresis. CS-TPP-dsRNA nanoparticles were exposed to lumen contents collected from *Aedes aegypti* larvae. At 1, 3, 6, 12 and 24 h after exposure, the samples were collected and resolved on 1% agarose gels. The gels were stained with GelRed® and photographed under UV light. M, 1 Kb ladder and NPs CS-TPP-dsRNA nanoparticles. Pictures of entire gel are included.

FIG. 3 shows fluorescence microscope analysis of the distribution of FITC labeled CS-TPP nanoparticles in mosquito larvae. CS-TTP-dsRNA nanoparticle labeled with FITC fluorescein dye were fed to mosquito larvae. At 24 h after initiation of feeding nanoparticles, the midgut and epidermis with fat body attached were dissected. The tissues were washed with IX PBS buffer and fixed with 4% paraformaldehyde. Tissues were stained with mounting medium containing DAPI were visualized under Nikon ECLIPSE 90i fluorescence microscopy. White and red arrows indicate fat body (FB) and epidermis (Epi) tissues, respectively. (Scale bar=50 μm).

FIGS. 7A-7F illustrate interactions between EGCG, dsRNA and PLL nanoparticles. Zeta potential of: FIG. 7A—EGCG-dsRNA complex, PLL-dsRNA nanoparticles with and without EGCG, FIG. 7B—Size distribution of PLL/EGCG-dsRNA nanoparticles, FIG. 7C—The binding of EGCG-dsRNA and PLL/EGCG-dsRNA causes the exclusion of EB from dsRNA and the quenching of EB fluorescence. FIG. 7D—Transmission electron microscopy analysis of PLL/EGCG-dsRNA nanoparticles (Scale bar=100 nm). FIG. 7E—In vitro release profile of dsRNA from PLL-dsRNA and PLL-EGCG-dsRNA in phosphate buffered saline (pH=8.0). FIG. 7F—Formation of PLL-EGCG-dsRNA nanoparticles in gel retardation assay.

FIG. 8A: Knockdown efficiency of PLL-EGCG-dsRNA polyplexes testing the luciferase activity in Sf9 cells expressing the luciferase gene; FIG. 8B: CypHer-5E-labeled dsRNA conjugated to PLL-EGCG nanoparticle reduce the accumulation of dsRNA in the acidic bodies of Sf9 cells. FIG. 8C: Cellular uptake efficiency of polyplexes in Sf9 cells; FIG. 8D: Gene silencing efficiency of PLL/EGCG-dsRNA nanoparticles in the presence and absence of EGCG on Aag-2 cells for 72 h. (data represented as the mean±S.D. (n=5).

FIG. 10A: Cy-3 dsRNA containing polyplexes fed mosquito larvae viewed under fluorescence microscope; FIG. 10B: confocal microscope analysis of biodistribution and internalization of Cy-3 labeled dsRNA polyplexes in mosquito larvae (midgut and epidermis with fat bodies cells); FIG. 10C: $^{32}$P labeled dsRNA polyplexes processing siRNA in mosquito larvae by pellet feeding assay. FIG. 10D: Mortality induced by orally delivered polyplexes in mosquito larvae. Mortality was scored on before pupation. Mean±SE (n=3) are shown. FIG. 10E: Polyplexes induced morphological changes in mosquito larvae by feeding. FIG. 10F: Knockdown efficiency of polyplexes were fed to the mosquito larvae. The knockdown of IAP, SSK, SNF7, SRC, MET and JHAMT gene levels were quantified on 3$^{rd}$ day post feeding. Mean±SE (n=5) are shown.

FIG. 23A includes the results of DLS analysis of PS:Cf:dsRNA nanoparticles z-average size and zeta potential. FIG. 23B illustrates the formation of nanoparticles (PS-Cf-dsRNA) as verified using a gel retardation assay.

FIG. 24A includes morphological characterization of polyplexes in TEM image. FIG. 24B includes higher magnification of single particles in STEM image. FIG. 24C includes elemental analysis of polyplex. (Scale bar=a) 100 nm; b) 10 nm and c) 10 nm).

DESCRIPTION OF EXEMPLARY EMBODIMENTS

Figure 1A:
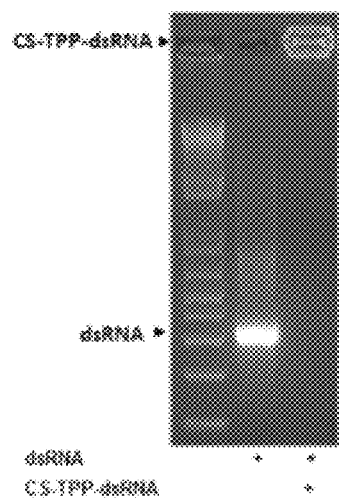
FIGS. 1A-1E relate to preparation and characterization of CS-TPP-dsRNA nanoparticles.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes compositions and methods for improving RNA interference (RNAi) efficiency in insects. In particular, certain embodiments of the presently-disclosed subject matter relate to use of nanoformulations of double-stranded RNA (dsRNA) to limit nuclease degradation of the dsRNA, and enhance cellular update and intracellular transport to improve delivery of the dsRNA to enhance RNAi in insects.

In some embodiments, the composition includes a double stranded RNA (dsRNA) molecule for initiating RNA interference (RNAi) in an insect, and a delivery-enhancing agent, assembled with the dsRNA in a nanoparticle.

In some embodiments, the delivery-enhancing agent includes (−) epigallocatechin-3-O-gallate (EGCG). In some embodiments, the delivery-enhancing agent also includes a polymer.

In some embodiments, the polymer is a polyamino acid. In some embodiments, the polymer is selected from the group consisting of: polylysine, polyargenine, polyhistodine and other polyamino acids. In some embodiments, the ratio of polymer to EGCG is from about 1:10 to about 10:1. In some embodiments, the ratio of polymer to EGCG is about 1:3.

In some embodiments, the delivery-enhancing agent includes Chitosan (CS) and a cross-linker as components of the delivery enhancing agent. In some embodiments, the cross-linker is sodium tripolyphosphate, dextran sulfate, or poly-D-glutamic acid. In some embodiments, the ratio of CS to cross-linker is from about 4:1 to about 6:1.

In some embodiments, the delivery-enhancing agent includes protamine sulfate (PS) as a component of the delivery enhancing agent. In some embodiments, the delivery-enhancing agent also includes a cationic-lipid formulation for transfecting insect cells. In some embodiments, the cationic-lipid formulation is CELLFECTIN® or CELLFECTIN® II.

In some embodiments, the nanoparticle of the composition has a mean size equal to or less than about 200 nm.

In some embodiments, the dsRNA of the composition encodes a polypeptide, or a fragment thereof, selected from the group consisting of inhibitor of apoptosis (IAP), vacuolar-sorting protein SNF7 (SNF7), snakeskin (SSK), and off-track (OTK), and combinations thereof.

The presently-disclosed subject matter further includes a method of inducing RNAi in a cell, comprising: contacting the cell with the composition as disclosed herein. In some embodiments, the cell is in an insect. In some embodiments, the insect is a mosquito. In some embodiments, the insect is an Asian longhorn beetle. In some embodiments, the insect is a fall armyworm.

In some embodiments, the method includes contacting the cell with the composition suppresses expression of one or more genes selected from the group consisting of dsIAP, dsSNF7, dsSSK, dsOTK, and combinations thereof.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

In certain instances, nucleotides and polypeptides disclosed herein are included in publicly-available databases, such as GENBANK© and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

The present application can "comprise" (open ended) or "consist essentially of" the components of the present invention as well as other ingredients or elements described herein.

As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments 20%, in some embodiments 10%, in some embodiments 5%, in some embodiments 1%, in some embodiments 0.5%, in some embodiments 0.1%, in some embodiments 0.01%, and in some embodiments 0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples. The following examples may include compilations of data that are representative of data gathered at various times during the course of development and experimentation related to the present invention.

EXAMPLES

Example 1

As illustrated by studies summarized herein, RNA interference-based control measures are effective in increasing the mortality of *Aedes Aegypti* mosquito larvae.

In this Example, Chitosan (CS) was cross-linked to sodium tripolyphosphate (TPP) to produce nano-sized polyelectrolyte complexes with dsRNA. CS-TPP-dsRNA nanoparticles were prepared by ionic gelation method. The encapsulation efficiency, protection of dsRNA from nucleases, cellular uptake, in vivo biodistribution, larval mortality and gene knockdown efficiency of CS-TPP-dsRNA nanoparticles were determined. The results showed that at a 5:1 weight ratio of CS-TPP to dsRNA, nanoparticles of less than 200 nm mean diameter and a positive surface charge were formed. Confocal microscopy revealed the distribution of the CS-TPP-dsRNA nanoparticles in midgut, fat body and epidermis of yellow fever mosquito, *Aedes aegypti* larvae. Bioassays showed significant mortality of larvae fed on CS-TPP-dsRNA nanoparticles. These assays also showed knockdown of a target gene in CS-TPP-dsRNA nanoparticle fed larvae. These data suggest that CS-TPP nanoparticles may be used for delivery of dsRNA to mosquito larvae.

Synthesis of CS-TPP-dsRNA Nanoparticles.

The CS-TPP-dsRNA nanoparticles were prepared by ionic gelation method using the negatively charged phosphate groups of TPP to cross-link with the positively charged amino groups of CS. First, the formation of CS-TPP nanoparticles was investigated. Visual inspection of the solution results in one of the following: a clear solution when CS and TPP levels are low, and opalescent suspension when CS and TPP concentrations are median, and spontaneous aggregations under high CS and TPP concentrations. These results suggested that the formation of suitable nanoparticles only occurs at specific concentrations of CS and TPP[26, 27, 28].

CS-TPP ratios of 1:1, 3:1, 5:1 and 7:1 were tested for tested for synthesis of nanoparticles. During the synthesis of nanoparticles, the ratio of CS-TPP was determined so that the smallest size and positive charge are created to facilitate the interaction with cell membranes. The size, zeta potential, and PDI were measured by DLS. The CS and TPP particles exhibited size reduction and increasing mass ratio as the mean diameter of the particles decreased from 243 nm to 126 nm. It has been reported that larger particles at a lower ratio to the cross-linking of several smaller mono-particles yield an overall larger cluster in solution[29]. The surface charge and mass ratio of the particles were found to increase from +1.97 to +65 mV and 1:1 to 7:1, respectively. This indicates that there are unbound amino groups present, even at the low 1:1 mass ratio, revealing a positive zeta potential over the entire molar range[30]. It may also reveal the surface charge of TPP[27].

To investigate the preparation of CS-TPP-dsRNA nanoparticles by ionotropic gelation, methods similar to those previously described were followed for the development of siRNA, protein, peptides, and drug molecule nanoparticles[31,32,33,34,35]. dsRNA incorporation into CS-TPP nanoparticles based on the surface charge and size was explored. Comparatively, CS-TPP-dsRNA nanoparticles increased in size and decreased in surface charge as measured by DLS analysis. The formation of CS-TPP-dsRNA nanoparticles was analyzed using gel retardation assay. The dsRNA was not efficiently complexed with CS-TPP and migrated faster at the CS-TPP ratio of 1:1. In contrast dsRNA complexed well and showed a retarded migration and stayed in the well at ratios of 3:1, 5:1 and 7:1. The results showed that 3:1, 5:1 and 7:1 ratios produced CS-TPP-dsRNA complexes. This may be due to the formation of nanoparticles in a process derived from inter and intramolecular linkages facilitated by the anionic molecules[36]. The nanoparticles produced by mixing at 3:1, 5:1 and 7:1 ratios were tested in Aag-2 mosquito cell line. The nanoparticles produced by 7:1 ratio caused a decrease in the cell viability and affected cell morphology. This may be due to the strong electrostatic interaction between the cell membranes and positively charged nanoparticles[37]. Therefore, only nanoparticles with an N/P ratio equal to 5:1 were used in subsequent experiments.

Characterization of CS-TPP-dsRNA Nanoparticles.

Figure 1B:
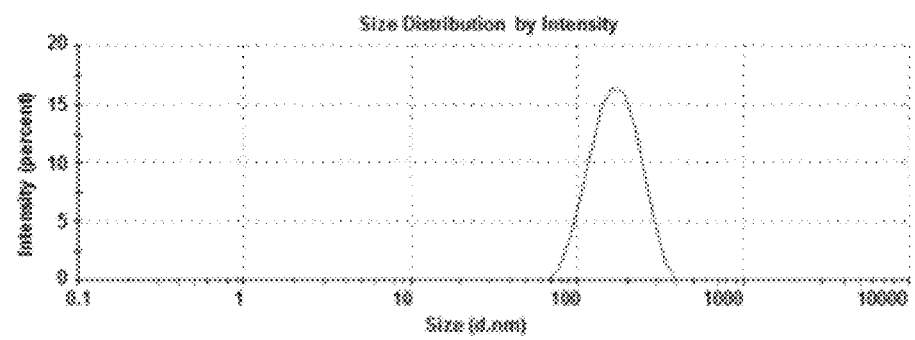
Figure 1C:
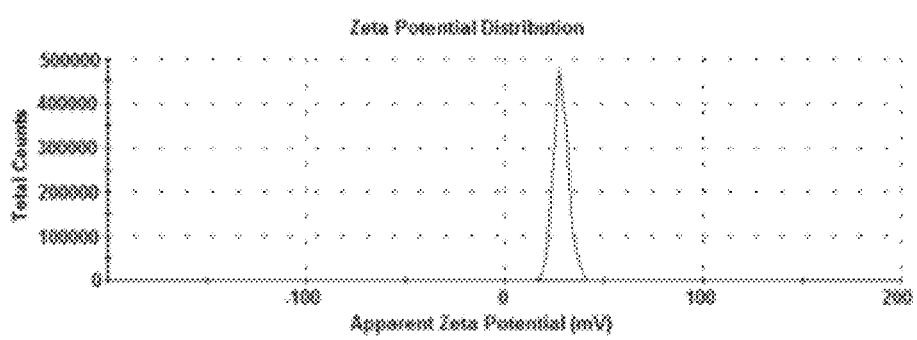
Figures 1D, 1E:
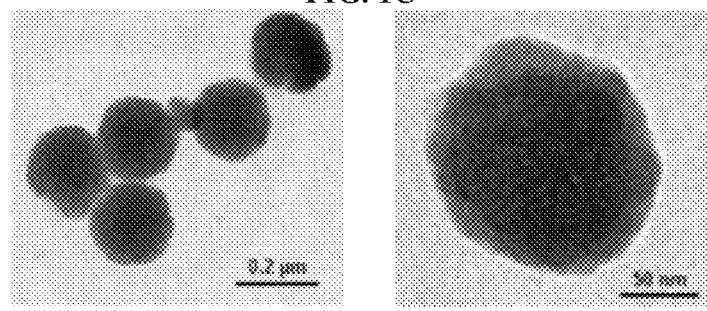

Gel retardation assays of the CS-TPP-dsRNA nanoparticles prepared showed efficient incorporation of dsRNA into nanoparticles (FIG. 1A). The mean particle size of CS-TPP-dsRNA is less than 200 nm and a lower PDI of 0.207 as determined by Zetasizer (FIG. 1B). The surface charge of CS-TPP-dsRNA nanoparticles is +34.37±0.94 mV (FIG. 1C). The TEM images of CS-TPP-dsRNA nanoparticles showed a spherical structure (FIGS. 1D and 1E). The possibility of nanoparticles modifying the surface morphology is of particular importance for in vivo applications. It has previously been reported that particles in the nanometer size and of the spherical structure have a relatively higher intracellular uptake compared to microparticles[38]. In the studies, approximately 80% entrapment efficiency was observed as measured by UV-visible spectrophotometry. Previous studies showed that the entrapment efficiency of siRNA loaded onto nanoparticles decreased significantly by increasing CS concentration. Inefficient siRNA entrapment was noted when higher concentration of CS was used as the viscous solution restricted the association of the siRNA 39. The low entrapment efficiency of nanoparticles may be due to interference shielding effects, which affect the interaction between nucleic acid and amino groups of CS[40].

One of the most important factors governing RNAi efficiency is the capacity of a carrier system to protect dsRNA from nuclease degradation. To investigate the nuclease protection ability of CS-TPP-dsRNA nanoparticles, the nanoparticles prepared were exposed to the lumen contents of the alimentary canal dissected from mosquito larvae. The nucleases present in the lumen of mosquito larvae degraded naked dsRNA within one hour of exposure. In contrast, the CS-TPP-dsRNA nanoparticles protected dsRNA from nuclease degradation up to 24 h (FIG. 2A). Also, dsRNA was dissociated from CS-TPP nanoparticles with the help of heparin (1000 U-ml). The dsRNA stability was analyzed by gel electrophoresis. As shown in FIG. 2B, the dsRNA in CS-TPP-dsRNA complexes was protected from digestion by nucleases.

CS-TPP-dsRNA nanoparticles were stored at various temperatures of 4° C., 25° C. and 37° C. in deionized water up to 10 days and analyzed by gel electrophoresis. No reduction CS-TPP-dsRNA complexes was detected. A previous study revealed that cross-linkers could enhance the stability of particulates[42]. Nanoparticle size significantly increased after 10 days of storage. These results are similar to reports on CS-TPP-siRNA nanoparticles, which exhibited only a slight increase in particle size after 15 days of storage[24]. The release profile of dsRNA from CS-TPP was studied in PBS at pH 7.4 up to 60 h. dsRNA was rapidly released during first 30 h, which resulted in a 39% cumulative release of dsRNA. After 30 h, the dsRNA was slowly released up to 60 h, resulting in a 55% cumulative dsRNA release. Cross-linking may be responsible for the strong interaction between CS-TPP-dsRNA nanoparticles.

In Vivo Distribution of CS-TPP-dsRNA Nanoparticles.

Figure 4:
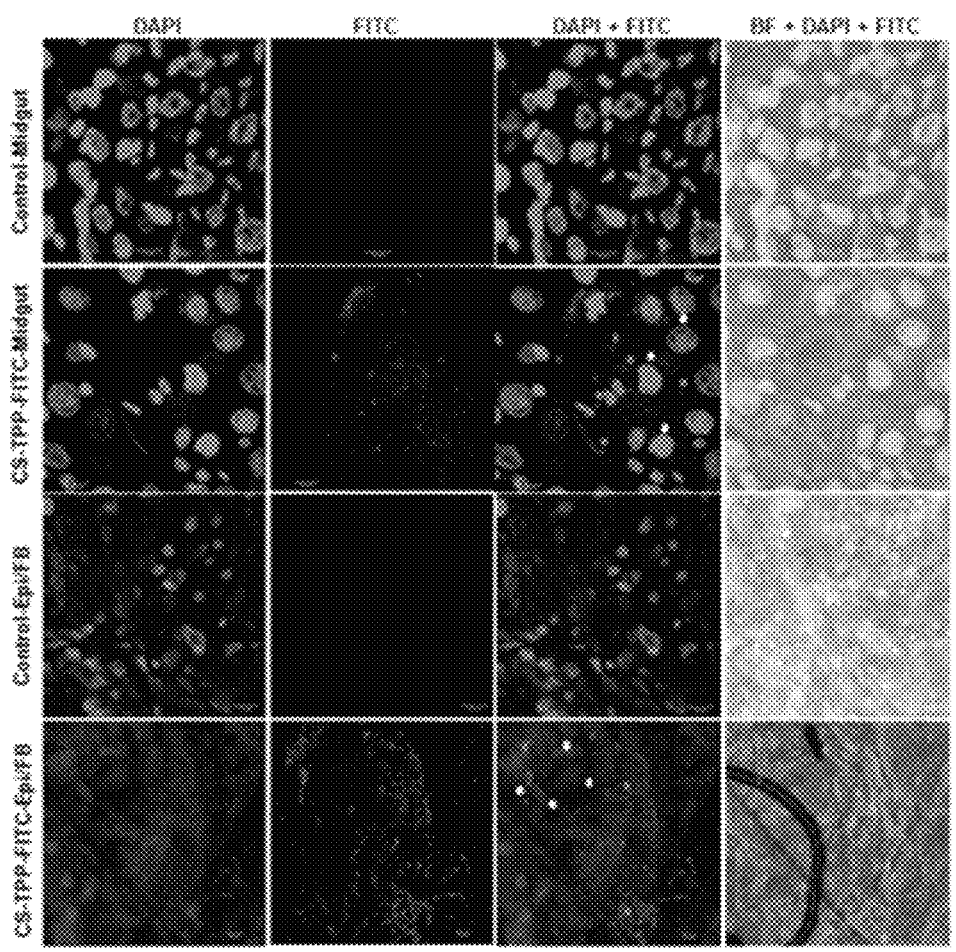
FIG. 4 shows confocal microscope analysis of biodistribution of FITC labeled CS-TPP nanoparticles in mosquito larvae. CS-TTP-dsRNA nanoparticles conjugated with FITC fluorescein dye were fed to mosquito larvae. At 24 h after initiation of feeding nanoparticles, midgut and epidermis with fat body attached were dissected. The tissues were washed with 1×PBS buffer and fixed with 4% paraformaldehyde. Tissues were stained with mounting medium contains DAPI and visualized under 63× magnification of Leica SP8 confocal microscope. The white and red arrow indicates nucleus and nanoparticles, respectively. (Scale bar=20 μm (A, B, C) and 5 μm (D).

An overall positive charge of the nanoparticle complex formed under optimal conditions fosters cell attachment, followed by membrane fusion via endocytosis, and ultimately endosomal escape by proton sponge effect[43]. Cellular uptake and in vivo distribution of nanoparticles in mosquito larvae were studied using FITC-labeled CS-TPP-dsRNA nanoparticles. The FITC-labeled nanoparticles were fed to *Aedes aegypti* larvae and tissues were dissected at 24 h after feeding nanoparticles. The tissues were washed, fixed and visualized under both compound and confocal microscopes. FITC-labeled nanoparticles were detected in fat body attached to the epidermis and midgut cells. These data suggest that nanoparticles fed to larvae were internalized by midgut cells and tissues such as the fat body and epidermis (FIG. 3). Tissues dissected from FITC-labeled nanoparticles observed under a confocal microscope showed green signals representing FITC-labeled nanoparticles in the midgut, epidermis and fat body cells (FIG. 4). Conversely, the tissues dissected from FITC-fluorescein fed larvae alone did not show any such signals (FIG. 4). Previous studies showed that both positively and negatively charged nanoparticles were distributed throughout the larval body, but positively charged nanoparticles showed faster attachment or internalization in tissues. Indeed, positively charged nanoparticles were present in the gastrointestinal tract within the gastric caeca. Although negatively charged nanoparticles were detected even after adult metamorphosis in tissues associated with the head, body parts, and ovaries, in vitro studies found that positively charged nanoparticles were more effective than negatively charged nanoparticles in mosquito larvae[44,45]. The data showing the distribution of positively charged nanoparticles in the midgut, fat body and epidermis are in line with these published reports. In mammalian cells, positively charged nanoparticles are internalized more efficiently than negatively charged nanoparticles due to their electrostatic interactions with the plasma membrane[46]. Indeed, positively charged CS-TPP nanoparticles were shown to deliver nucleic acids into HeLa cells[38].

The Efficacy of CS-TPP-dsRNA Nanoparticles.

Figure 5:
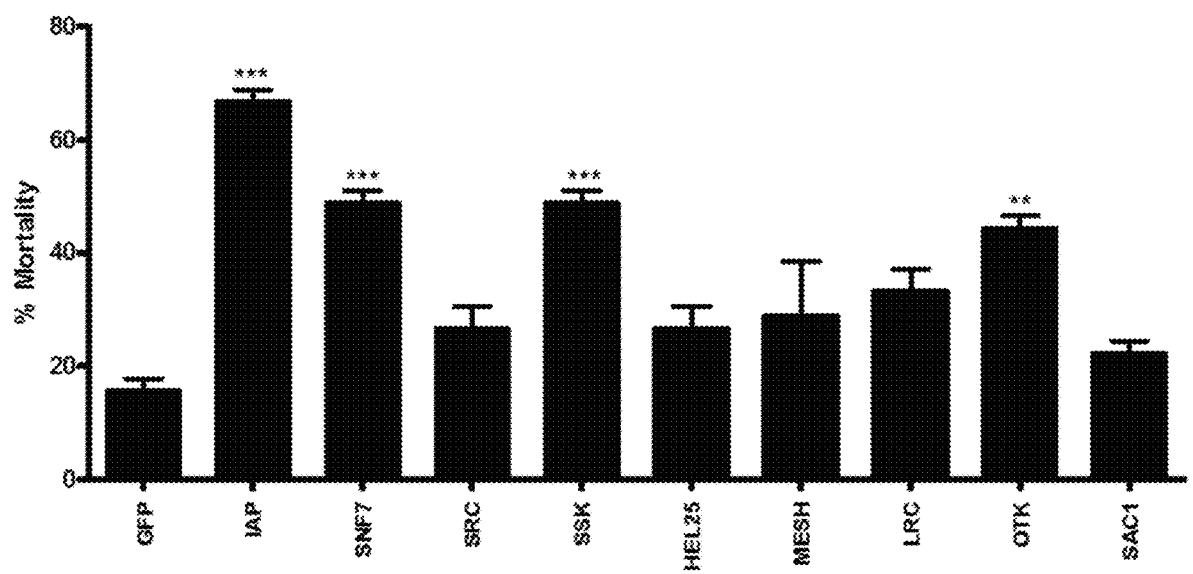
FIG. 5 illustrates screening candidate genes to control mosquito larvae by delivering dsRNA conjugated to CS-TPP nanoparticles. Mosquito larvae were fed on CS-TPP-dsRNA nanoparticles containing dsRNA targeting one of nine selected genes or GFP. Mortality was recorded on the 10th day after initiation of feeding. Mean±S.E (n=3). The asterisks above the bar indicate the significance of difference (One-way ANOVA, Turkey's test $P=<0.05$, ; *, $P=<0.001$). GFP, green fluorescent protein; IAP, inhibitor of apoptosis; SNF7, vacuolar-sorting protein; SRC, steroid receptor co-activator; SSK, Snakeskin; HEL25E, Helicase at 25E; MESH, membrane-spanning protein; LRC, leukocyte receptor complex member; OTK, off-track; SAC1, suppressor of actin.
Figure 6:
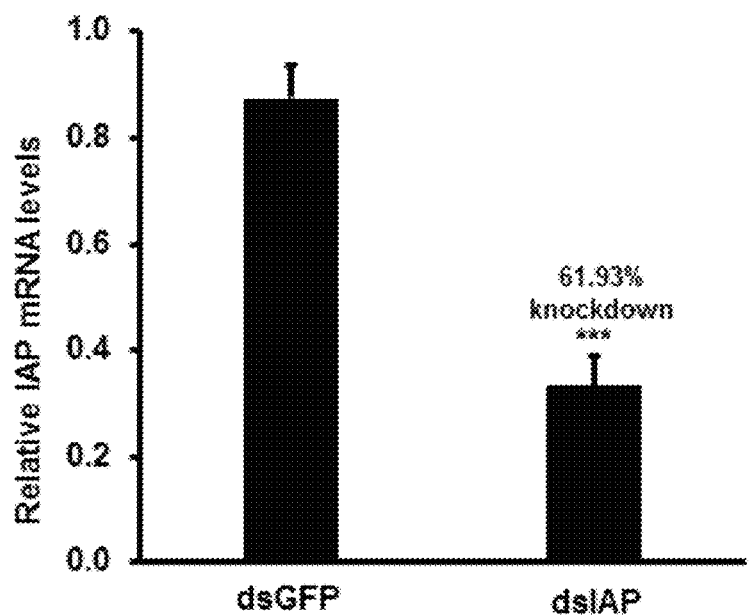
FIG. 6 shows how CS-TPP-AaIAP dsRNA knocks down AaIAP gene. Knockdown of AaIAP gene was analyzed in mosquito larvae fed with CS-TPP-dsIAP or CS-TPP-dsGFP nanoparticles by qRT-PCR. Five days after feeding CS-TPPdsIAP nanoparticles to *Aedes aegypti* larvae, the RNA was isolated, converted to cDNA and used in qRT-PCR to determine relative IAP mRNA levels. Data are presented as mean±SE. (n=3). The asterisks above the bar indicate the significance of difference (One-way ANOVA, Turkey's test ***, P=<0.001).

The effectiveness of CS-TPP-dsRNA nanoparticles in silencing target genes and killing mosquito larvae was tested. Nine candidate genes were selected based on their effectiveness in triggering RNAi in *Aedes aegypti*, and other insects tested. The dsRNA prepared using fragments of nine selected genes and the gene coding for enhanced green fluorescence protein (EGFP) as a control were used to prepare CS-TPP-dsRNA nanoparticles. The nanoparticles, mosquito larval food, and agarose were used to prepare food pellets. The food pellets were fed to larvae once a day until pupation. The mortality caused by CS-TPP-dsRNA nanoparticles varied from 20-65%. The control larvae fed on CS-TPP-dsEGFP showed 18% mortality. The CS-TPP-dsRNA nanoparticles targeting IAP, SNF7, SSK, and OTK caused significantly higher mortality when compared to the mortality caused by control CS-TPP-dsGFP nanoparticles (FIG. 5). Further, the gene knockdown by CS-TPP-dsIAP nanoparticles was confirmed using reverse-transcriptase quantitative real-time PCR (RT-qPCR). The larvae were fed food pellets containing nanoparticles once daily until pupation. The mRNA transcript levels of target genes were quantified on the fifth day after the first feeding event. Oral administration of nanoparticles reduced the target gene mRNA levels by 62% (FIG. 6). The qRT-PCR results showed that mosquito larvae that were fed CS-TPP-dsIAP effectively triggered RNAi. These results suggest that feeding mosquito larvae CS-TPP-dsRNA nanoparticles can deliver dsRNA to their cells, resulting in uptake of dsRNA and suppression of target gene expression. The IAP gene from *Bombyx mori* was identified and shown to function as a caspase inhibitor to block apoptosis[47]. The IAP1 gene was identified in *Aedes aegypti* and showed that the gene product inhibits both initiator and effector caspases[48]. In Aag-2 cell, five genes coding for IAPs (1, 2, 5, 6 and 9) were identified. Treating these cells with dsRNA targeting these genes caused a significant reduction in target gene mRNA levels, but only dsIAP1 induced apoptosis phenotype[49]. Application of dsIAP gene caused mortality in *Lygus lineolaris Halyomorpha halys, Agrilus planipennis* and *Anoplophora* glabripennis[50,51,52,53].

The previous studies[20,21,22,54] used CS nanoparticles to deliver dsRNA to silence genes in insects, including *Aedes aegypti*. However, the knockdown efficiency and mortality achieved by CS-mediated delivery of dsRNA were not very high; therefore, these nanoparticles are not widely used to deliver dsRNA to mosquitoes and other insects. In previous studies in *Aedes aegypti* larvae, CS nanoparticle-based delivery of dsRNA caused less than 50% knockdown of the target gene and larval mortality[54]. In this study, CS-TPP-dsRNA nanoparticles were found to be better than CS nanoparticles in delivering dsRNA to mosquito larvae. In future studies, it may be possible to achieve up to 100% mortality of larvae after modifying strong bond interaction of nanoparticles and identifying an effective target gene. Work is in progress to screen and identify effective target genes and to determine the best delivery system to achieve 100% mortality in *Aedes aegypti* larvae after delivery of dsRNA using nanoparticles.

Visual Inspection of CS-TPP Nanoparticles Formation.

The formation of CS-TPP nanoparticles was examined by visual inspection[27,28]. A preliminary test was done to determine the optimum conditions required for the formation of nanoparticles. In this regard, medium molecular weight CS (75-85% deacetylated) was dissolved in 1% acetic acid (w/v) to prepare 10 mg/ml solution. The TPP was dissolved in deionized water (0.25-1.5 mg/ml). Visualization of the nanoparticle formation was carried out by addition of 2 ml of TPP solution to 5 ml of CS solution under magnetic stirring at room temperature.

Nanoparticles Preparation.

CS-TPP-dsRNA nanoparticles were formed using the ionic gelation method. Nanoparticles were prepared by adding 1 ml of TPP aqueous solution (1 mg/ml) and 1 ml of dsRNA (0.250 mg/ml) in deionized water in a dropwise manner to 5 ml of CS solution (1 mg/ml) under magnetic mixing at room temperature. The nanoparticles were then incubated for 30 min at room temperature. Nanoparticles were collected by centrifugation at 13,000×g for 10 min. The supernatant was removed, and the pellet was washed three times with deionized water and resuspended in milliQ water. The nanoparticles were then sonicated for 5 min in an ultrasonic liquid processor and used for further analysis.

Gel Retardation Assay.

The binding affinity of dsRNA to CS-TPP nanoparticles was confirmed by agarose gel electrophoresis using a 1 kb DNA ladder for size reference. Naked dsRNA and CS-TPP nanoparticles were used as positive and negative controls, respectively. The CS-TPP-dsRNA nanoparticles were loaded onto 1% agarose gels stained with GelRed® (Biotium, USA). After electrophoresis, the gel was photographed with an Alpha Imager™ Gel Imaging System (Alpha Innotech, San Leandro, Calif.) under ultraviolet light.

Dynamic Light Scattering (DLS) Analysis.

The mean particle size (z-average), surface charge (zeta potential) and polydispersity (PDI) of CS-TPP-dsRNA nanoparticles were measured by photon correlation spectroscopy (PCS) using Zetasizer (Malvern Instruments, UK). All measurements were made in triplicate at 25° C. and data are reported as mean±standard deviation.

TEM Imaging of CS-TPP-dsRNA Nanoparticles.

To determine the morphology of the nanoparticles, the particles were viewed under a transmission electron microscope (TEM). A drop of CS-TPP-dsRNA nanoparticles was fixed on a copper microgrid that was natively stained with 2% phosphotungstic acid. The stained nanoparticles were incubated for 10 min at room temperature. The nanoparticles were then viewed under a TEM (HRTEM, JEOL 2010F, Japan) and images were captured.

Determination of dsRNA Loading Efficiency.

To determine the dsRNA loading efficacy of nanoparticles, the dsRNA conjugated with nanoparticles was separated from free dsRNA by centrifugation. The free dsRNA in the supernatants was measured by its absorbance at 260 nm wavelength using NanoDrop-2000 spectrophotometer (Thermo Fisher Scientific Inc., Waltham, Mass.). The amount of dsRNA incorporated within the nanoparticles was calculated by the difference between the initial quantity of dsRNA (Total dsRNA) and the remaining amount in the supernatant (Free dsRNA). The supernatant recovered from naked nanoparticles was used as a blank. Entrapment efficiency was calculated using the following method[55]:Entrapment efficiency=Total dsRNA−Free dsRNA/Total dsRNA× 100.

dsRNA Stability Assay.

To investigate ex vivo degradation, an assay described recently was used[56]. Mosquito larvae entire midgut was dissected and placed in 100 μl of 1×PBS and centrifuged for 10 min at 20,000×g. The supernatant was then collected and centrifuged in the same manner. Ten microliters of nanoparticles containing 1 μg of dsRNA were added to 10 μl (1 μg) of midgut extract and samples were collected at various time points (1, 3, 6, 12 and 24 h). Naked dsRNA was incubated in the midgut extract for 1 h as a control. The samples were resolved on a 1.0% (w/v) agarose gel, stained with GelRed® (Biotium, USA) and photographed with an Alpha Imager™ Gel Imaging System (Alpha Innotech, San Leandro, Calif.) under ultraviolet light.

Storage Stability of CS-TPP-dsRNA Nanoparticle Complexes.

CS-TPP-dsRNA nanoparticles were suspended in nuclease-free water and stored at 4° C., 25° C. and 37° C. for 10 days. Nanoparticle stability was determined by 1% agarose gel electrophoresis and nanoparticle size was measured at previously established time points.

In Vitro Release Studies.

The CS-TPP-dsRNA nanoparticles were incubated at room temperature (25° C.), in 2 ml of 1×PBS at pH 7.4. At certain intervals, (10, 20, 30, 40, 50, and 60 h) nanoparticles were centrifuged and 1.5 ml of the supernatant removed and replaced by 1×PBS solution. The amount of dsRNA released from the nanoparticles was determined using the NanoDrop-2000 spectrophotometer (Thermo Fisher Scientific Inc., Waltham, Mass.).

Biodistribution and Cellular Internalization of Nanoparticles.

In vivo, biodistribution and cellular internalization of nanoparticles were investigated using FITC-labeled nanoparticles. The FITC-labeled nanoparticles were prepared by following the method described previously[57]. Five mosquito larvae were placed in each well of 24-well plate containing 1 ml of nuclease-free water. FITC-nanoparticles were evenly mixed with mosquito larval food and embedded in 1% melted agarose. This food pellet was fed to mosquito larvae under dark conditions. After 24 h, the whole larvae were viewed under a fluorescence microscope. For biodistribution studies, mosquito larvae were dissected, the alimentary canal and fat bodies attached to the epidermis were collected and washed with 1×PBS. The tissues were fixed with 4% paraformaldehyde solution and incubated at 4° C. for overnight under dark conditions. The fixed tissues were mounted on the microscope slides stained with EverBrite™ mounting medium containing DAPI (Biotium, Inc. Fremont, Calif.) and examined under 63× magnification in a confocal laser-scanning microscope (Leica TCS SP8) using DAPI, Alexa Fluor 488 for FITC with 490-525 wavelength and bright field (BF) channels.

Mosquito Rearing.

*Aedes aegypti* (Waco strain) mosquitoes were reared as described previously[27]. Eggs were collected from lab colony adults and stored dry for approximately 2-4 weeks before hatching. Eggs were hatched in a 64 oz plastic pan containing 300 mL deoxygenated, filtered water inoculated with 10 mL of bovine live powder feeding solution (60 g/L). The pans were maintained in an incubator at 27±1.0° C. under a photoperiodic regime of 16:8 hour (L:D).

Freshly molted second-instar larvae were collected and briefly held in a separate pan containing filtered water before being transferred to 24-well plates for bioassays.

dsRNA Synthesis.

Nine candidate genes were selected based on previous studies of their efficacy as RNAi triggers[49,54,59,60]. The dsRNA targeting these genes was in vitro synthesized using the MEGAscript RNA synthesis kit (Ambion Inc., Foster City, Calif. USA) as described previously[55]. Briefly, 300-500 bp fragment of each gene was PCR amplified using gene-specific primers containing T7 RNA polymerase sequence at the 5' end. 500 ng of purified PCR product was used as a template in 20 μL in the vitro transcription reaction. The reaction mix was incubated for 16 h at 37° C., followed by 30 min of DNase I treatment. The reaction mixture was heat inactivated at 70° C. for 10 min and cool down slowly to room temperature. The dsRNA was precipitated by adding 0.1× volume of sodium acetate (3M, pH 5.2) and 2.5× the volumes of 100% ethanol and kept at −20° C. for at least 2 h. The reaction contents were then centrifuged at 4° C. for 15 min. The dsRNA pellet was rinsed with 75% ethanol and centrifuged again at 4° C. for 5 min. The ethanol was removed and the dsRNA pellet was dried and resuspended in milliQ water. The quality and quantity of dsRNA were checked by agarose gel electrophoresis and NanoDrop-2000 spectrophotometer (Thermo Fisher Scientific Inc., Waltham, Mass.), respectively.

Mosquito Feeding Assay.

Mosquito larval food containing nanoparticles was prepared by following methods described previously[20]. Briefly, 50 μl of nanoparticles containing 40 μg of dsRNA were mixed with 5 mg of bovine liver powder and added to 1.5% pre-melted agarose gel solution at 55° C. A group of 5-7-second instar larvae were transferred to each well of 24-well plate containing 1 ml of deionized water. Each treatment was replicated three times, and each experiment was repeated at least five times. The food pellet containing 40 μg of dsRNA was divided into three equal pieces and distributed to each well. Food containing dsRNA was added to pupae. Mortality was recorded until mosquito larvae in the control group became adults. The transcript levels of dsIAP target gene were determined on the 5th day after the first feeding of dsRNA.

Quantitative Real-Time PCR (RT-qPCR).

Total RNA was isolated from mosquito larvae using TRIzol reagent (Molecular Research Center Inc., Cincinnati, Ohio) following manufacturer's protocol. The total RNA was then treated with DNase I (Ambion Inc., Austin, Tex.). Two μg of total RNA was used for first strand cDNA synthesized using M-MLV Reverse Transcriptase (Invitrogen, USA). The first strand cDNA was used as a template for qPCR analysis. Each 10 μl qRT-PCR reaction contained 5 μl of Fast Start SYBR Green Master (Roche Diagnostics, Indianapolis), 2 μl of 1:2 diluted cDNA and 0.2 μl each of 10 μM forward and reversed gene-specific primers. An initial incubation of 95° C. for 3 min, followed by 40 cycles of 95 for 10 s, 55 for 20 s and 72 for 30 s settings, were used. Each experiment was replicated a minimum of three times using the samples from independent treatments. Relative expression levels of a target gene were determined using the reference gene, S7RP the $2^{-\Delta\Delta CT}$ method 58.

Statistical Analysis.

The nanoparticle cauterization data (size, charge, and PDI) are shown as the Mean±STD. The statistical significance of gene expression analysis for qRT-PCR was determined using t-test analysis. A one-way analysis of variance (ANOVA) was used to determine significance of larval mosquito mortality. P values of <0.05 were considered significant. The analyses were performed using GraphPad Prism 5 for windows.

Example 2

In this Example, (−) epigallocatechin-3-O-gallate (EGCG), dsRNA and poly-1-lysine (PLL) nanoparticles were prepared, characterized, and evaluated for their effectiveness in controlling *Aedes aegypti, Anoplophora glabripennis, Spodoptera frugiperda*. The nanoparticles prepared exhibited a uniform size, positive charge and spherical structure. These polycationic nanoparticles protected dsRNA from nuclease degradation and supported efficient cellular uptake and transport into Sf9 cells and Aag2 cells. Also, the dsRNA in the nanoformulations was processed to siRNA in larvae. In feeding bioassay, the nanoformulated dsRNA effectively silenced target genes and induced larval mortality. These studies not only developed methods to prepare PLL:EGCG:dsRNA nanoparticles, but also demonstrate their effectiveness in controlling mosquitoes, Asian longhorn beetles, and armyworms.

Preparation and Characterization.

Figure 11:
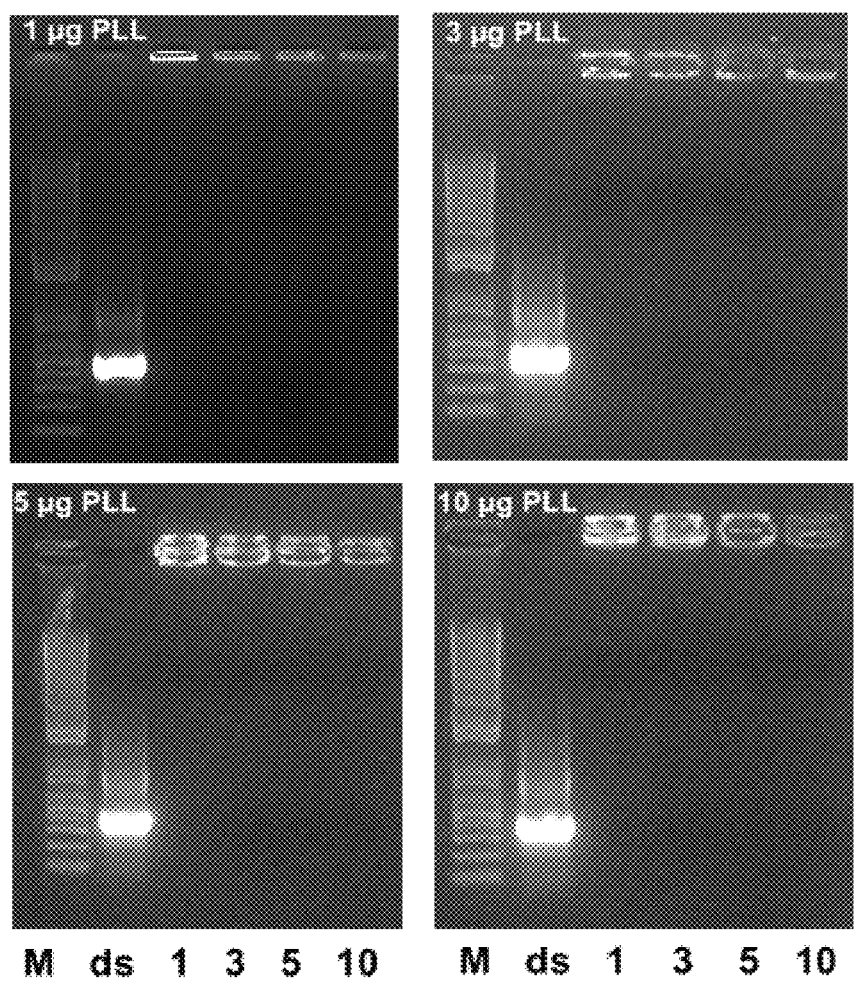
FIG. 11 The polyplexes prepared using 1 g dsRNA and varying concentrations of EGCG (1, 3, 5 and 10 µg) and PLL (1, 3, 5 and 10 µg) were evaluated by gel electrophoresis. The positively charged of PLL can neutralize the negative charges of the phosphate groups within the EGCG-dsRNA complexes, thus retarding the dsRNA mobility. Naked dsRNA was used as the control group. dsRNA bands decreased with increasing N/P ratios (from 1 to 10). This indicating that the negatively charged EGCG-dsRNA complexes could be neutralized entirely at this N/P value.

The PLL:EGCG:dsRNA nanoformualtion was prepared by self-assembly method which consists of EGCG-dsRNA complexes coated with a cationic polymer of PLL. The nanoparticles prepared using 1 μg dsRNA and varying concentrations of EGCG (1, 3, 5 and 10 μg) and PLL (1, 3, 5 and 10 μg) were evaluated by gel electrophoresis and DLS analysis (FIG. 11, Table 1).

Figure 7A:
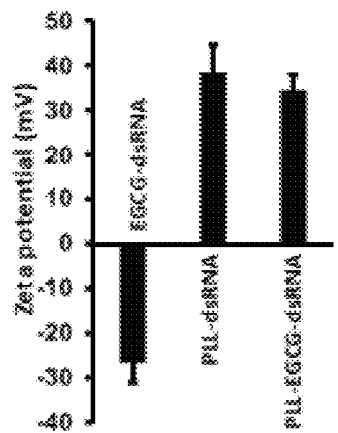
Figure 7B:
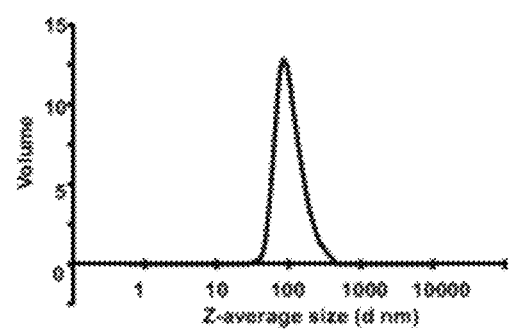
Figure 7C:
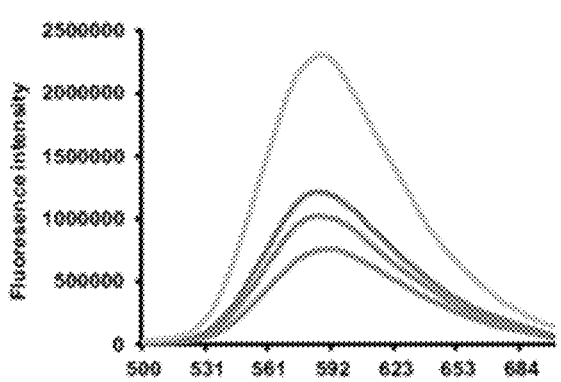
Figure 7D:
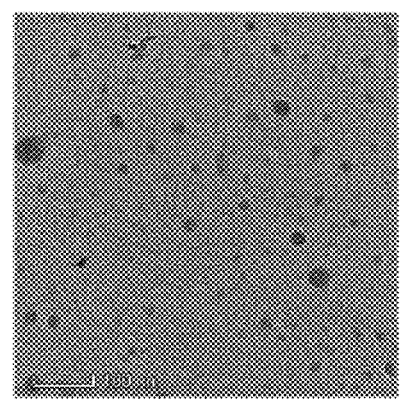
Figure 7E:
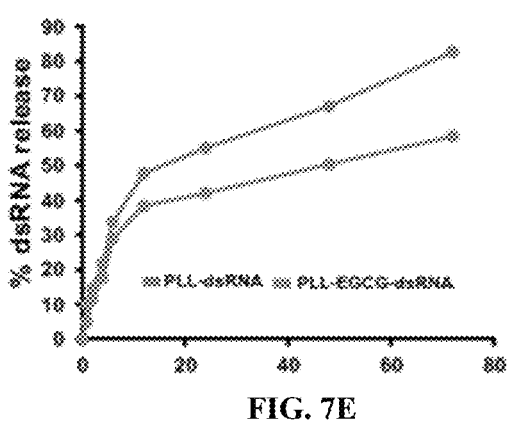
Figure 7F:
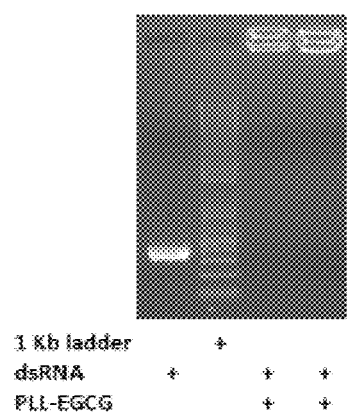
Figure 13:
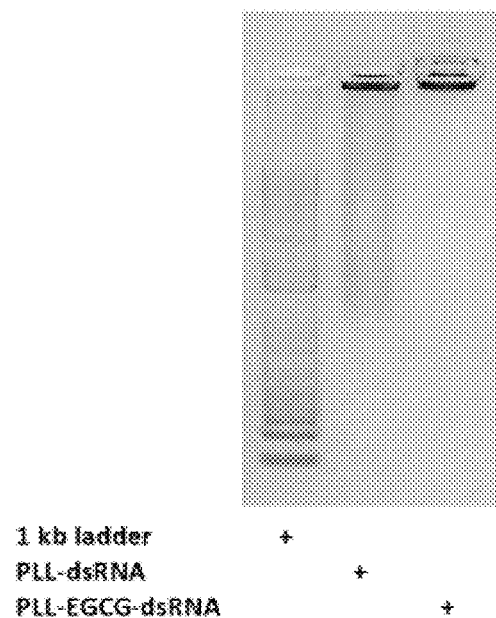
FIG. 13 shows PLL-dsRNA and PLL:EGCG:dsRNA checked in phosphate buffered saline solution (pH 8.0). After one hour samples were run on 1% agarose gel electrophoresis.

Table 1 includes information related to the characterization of PLL: EGCG:dsRNA polyplexes dsRNA loaded polyplexes, produced from different ratio of PLL and EGCG using self-assembly methods. Polyplexes size and surface charge was measured using Zetasizer (Malvern). The encapsulation efficiency was calculated from the following equation: Actual dsRNA loaded/theoretical dsRNA loaded× 10000 Different ratios of PLL:EGCG:dsRNA were tested in Sf9 cells. As shown results PLL:EGCG:dsRNA (5:3:1) ratio induced the highest knockdown of the luciferase activity.

improve the stabilization of polyplexes [84]. Further, dsRNA binding capacity of the polyplexes was assayed by gel retardation assay. Most of the dsRNA is present in the polyplexes (FIG. 7F). The size of the polyplexes was investigated by DLS and TEM. The results showed that most of the polyplexes were able to condense dsRNA into particles smaller than 100 nm in diameter. PLL:EGCG:dsRNA polyplexes were more stabilized than PLL:dsRNA ploplexes (FIG. 13). These results could be attributed to the enhanced binding affinity between EGCG and dsRNA, thus leading to the effective stabilization of the polyplexes. The stabilized, highly encapsulation and sustained release polyplexes are expected to support efficient gene silencing [92]. PLL: EGCG:dsRNA nanoparticles were tested in both in vitro and

TABLE 1

Characterization of PLL-DGCG-dsRNA Polyplexes

| S. No | PLL:EGCG:dsRNA | Size (d nm) | Zeta potential (mV) | Encapsulation efficiency (%) | Luciferase gene silencing (%) |
|---|---|---|---|---|---|
| 1 | 1:1:1 | 168.02 ± 2.3 | 16.54 ± 2.1 | 36.3 | 2.7 |
| 2 | 1:3:1 | 186.82 ± 4.5 | 13.36 ± 1.18 | 36.88 | 10.97 |
| 3 | 1:5:1 | 173.7 ± 5.6 | 11.1 ± 0.91 | 30.3 | 12.12 |
| 4 | 1:10:1 | 145.72 ± 8.1 | 8.18 ± 1.4 | 33.56 | N/A |
| 5 | 3:1:1 | 129.48 ± 2.8 | 27 ± 1.3 | 58.48 | 23.3 |
| 6 | 3:3:1 | 116.22 ± 3.6 | 24.7 ± 1.7 | 55.02 | 19.93 |
| 7 | 3:5:1 | 108.46 ± 4.1 | 22.18 ± 0.85 | 52.34 | 28.67 |
| 8 | 3:10:1 | 97.82 ± 6.3 | 19.52 ± 1.15 | 45.86 | N/A |
| 9 | 5:1:1 | 68.52 ± 1.7 | 38.4 ± 1.73 | 63.3 | 46.95 |
| 10 | 5:3:1 | 58.42 ± 2.3 | 36.6 ± 1.12 | 78.4 | 68.4 |
| 11 | 5:5:1 | 94.58 ± 4.2 | 34.4 ± 1.08 | 67 | 44.73 |
| 12 | 5:10:1 | 127.32 ± 2.5 | 32.48 ± 1.3 | 64.22 | N/A |
| 13 | 10:1:1 | 162.66 ± 1.8 | 51.4 ± 0.43 | 62.96 | 38.45 |
| 14 | 10:3:1 | 196.16 ± 2.6 | 50.62 ± 0.85 | 58.54 | 26.41 |
| 15 | 10:5:1 | 210.12 ± 4.3 | 48.52 ± 1.01 | 54.7 | 24.73 |
| 16 | 10:10:1 | 221.56 ± 2.9 | 46.26 ± 1.14 | 56.2 | N/A |

Figure 12A:
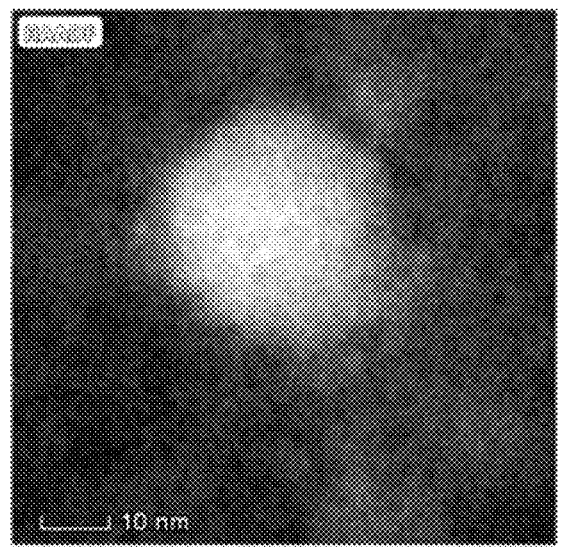
FIGS. 12A and 12B include results of transmission electron microscopy analysis of PLL/EGCG-dsRNA nanoparticles. a) Higher magnification of single particles in STEM image and b) Elemental analysis of nanoparticles. (Scale bar=a) 100 nm; b) 10 nm and c) 10 nm).
Figure 12B:
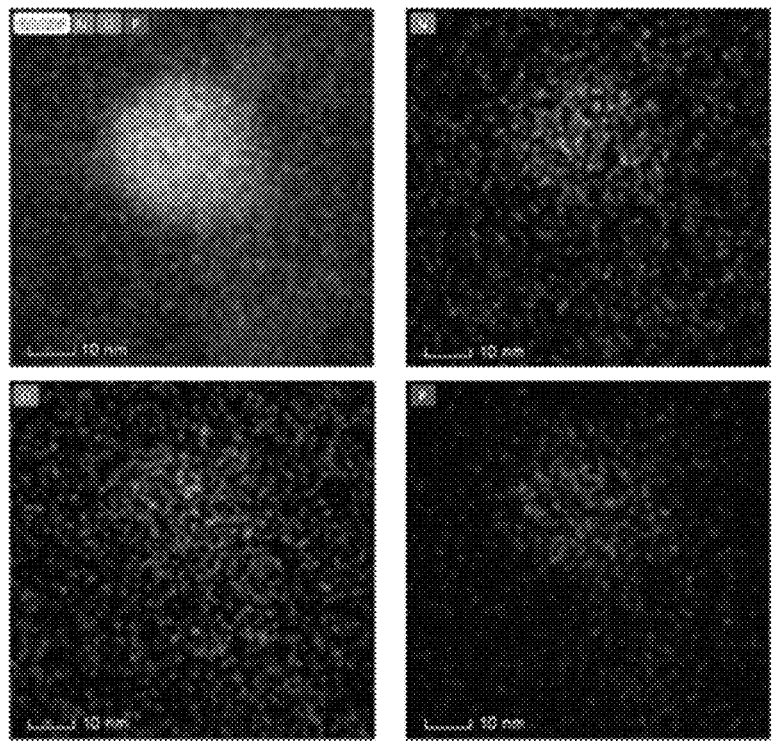

The zeta potential of PLL:dsRNA is 36.6±1.12 and that of EGCG:dsRNA is-26.6±0.88. However, adding PLL to EGCG:dsRNA formed nanoparticles with 34.2±1.48 zeta potential at a PLL:EGCG:dsRNA ratio of of 5:3:1 (FIG. 7A). The size and PDI of these nanoparticles are 58.4±2.33 and 0.19±0.032, respectively (FIG. 7B). Further, in ethidium bromide competitive binding assay, the fluorescence intensity of PLL:EGCG:dsRNA nanoparticles gradually decreased when compared to naked dsRNA (FIG. 7C). Observation under a transmission electron microscope (TEM) showed that the nanoparticles are spherical in shape and dispersed well and the size of the nanoparticles is consistent with the DLS results (FIG. 7D). The energy-dispersive X-ray spectroscopy (EDX) element mapping analysis showed (FIG. 12). The encapsulation efficiency of PLL:EGCG:dsRNA nanoparticles measured by spectrophotometer is 74±3.12% compared to --- for PLL:EGCG. The release rate of dsRNA from nanoparticles was sustained release in phosphate-buffered saline (pH 8.0) (FIG. 7E).

The self-assembly of polymer and polyphenol forms polyplexes which are stabilized by hydrophobic and electrostatic interactions [71, 86-91]. Competitive binding inhibition between dsRNA, EGCG and PLL is possible [84]. The polyanion, EGCG reduced the charge and size of the polyplexes. This could have been triggered by the neutralization of cationic polymers with anionic EGCG:dsRNA complexes. These results demonstrated that EGCG helps to in vivo to determine their ability to support efficient knockdown of target genes and RNAi response.

In Vitro Characterization.

Figure 8A:
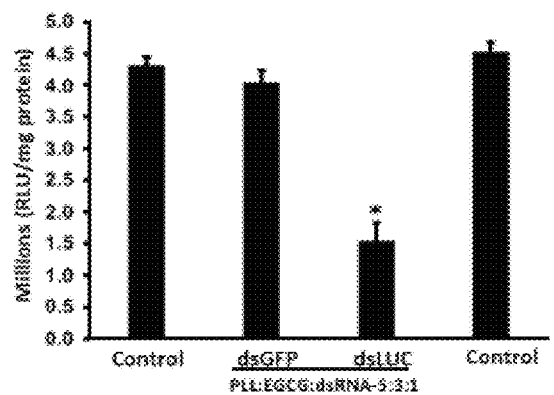
FIGS. 8A-8D illustrate PLL/EGCG-dsRNA functionality in vitro both Sf9 and Aag-2 cells.
Figure 8B:
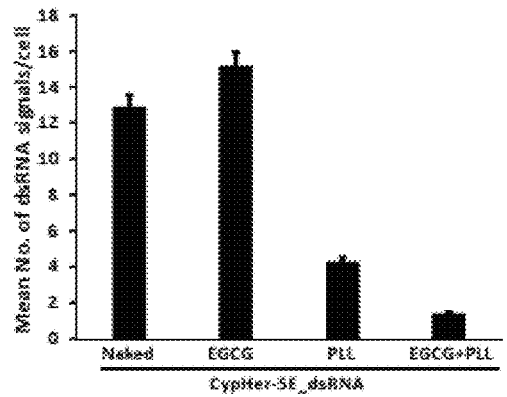
Figure 8C:
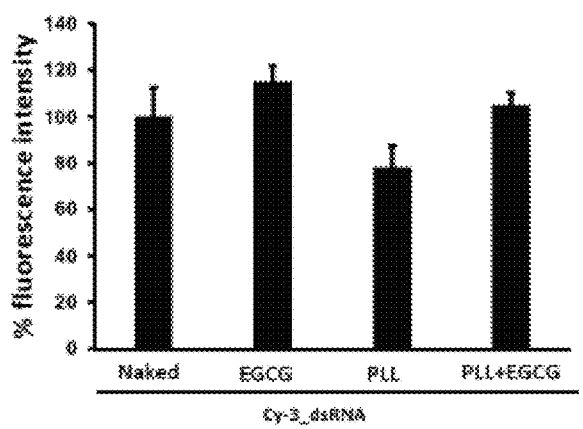
Figure 8D:
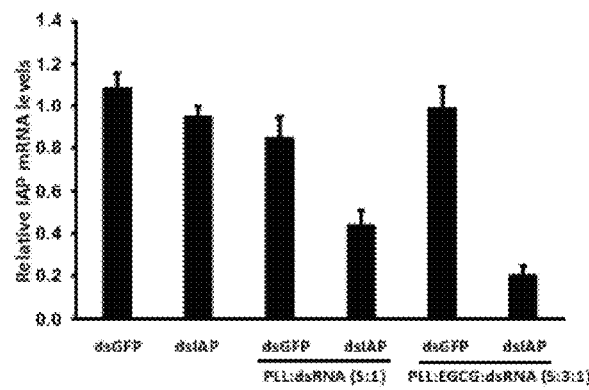
Figure 14:
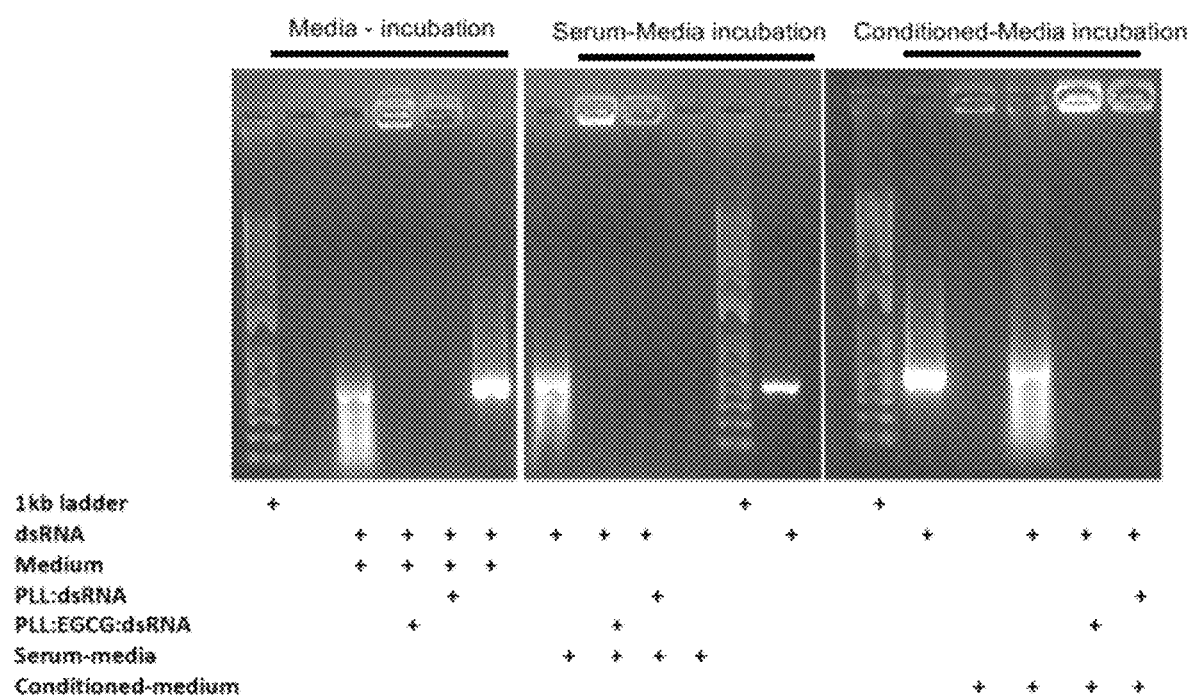
FIG. 14 includes results of dsRNA polyplexes stability assay. One microgram of dsRNA containing polyplexes incubated into media, serum containing media and conditional media. After one hour checked stability of nanoparticles in 1% agarose gel electrophoresis.
Figure 15:
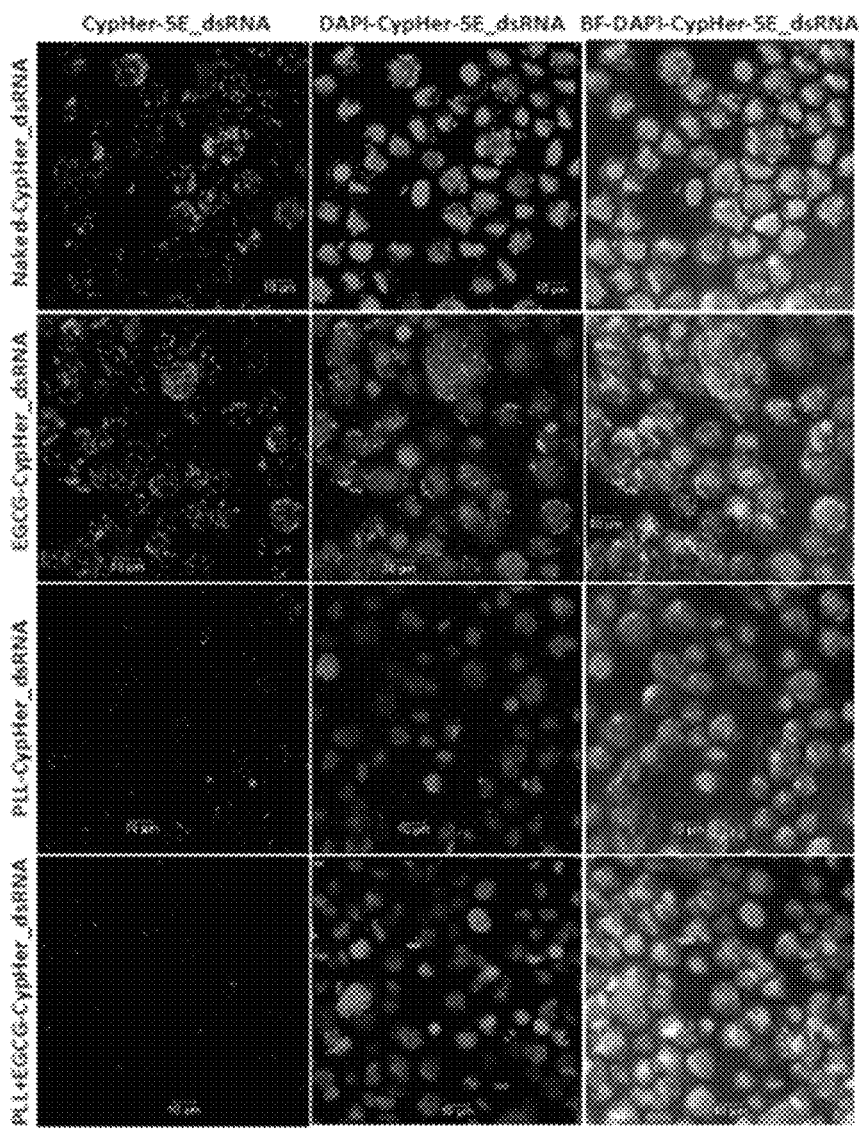
FIG. 15 illustrates that CypHer-5E-labeled dsRNA conjugated polyplexes reduce the accumulation of dsRNA in the acidic bodies of Sf9 cells. 120,000 cells/well were seeded in 8 well chamber slide and incubated 25 ng of naked, conjugated to EGCG, PLL and PLL-EGCG nanoparticle of CypHer-5E-labeled dsRNA mixed with Sf-900 II SFM medium for 4 h and washed the cells then fixed followed by stained using EverBrite mounting medium with DAPI and visualized the cells under Leica confocal microscope at 63× magnification (n=100; scale bar: 10 µm).
Figure 16:
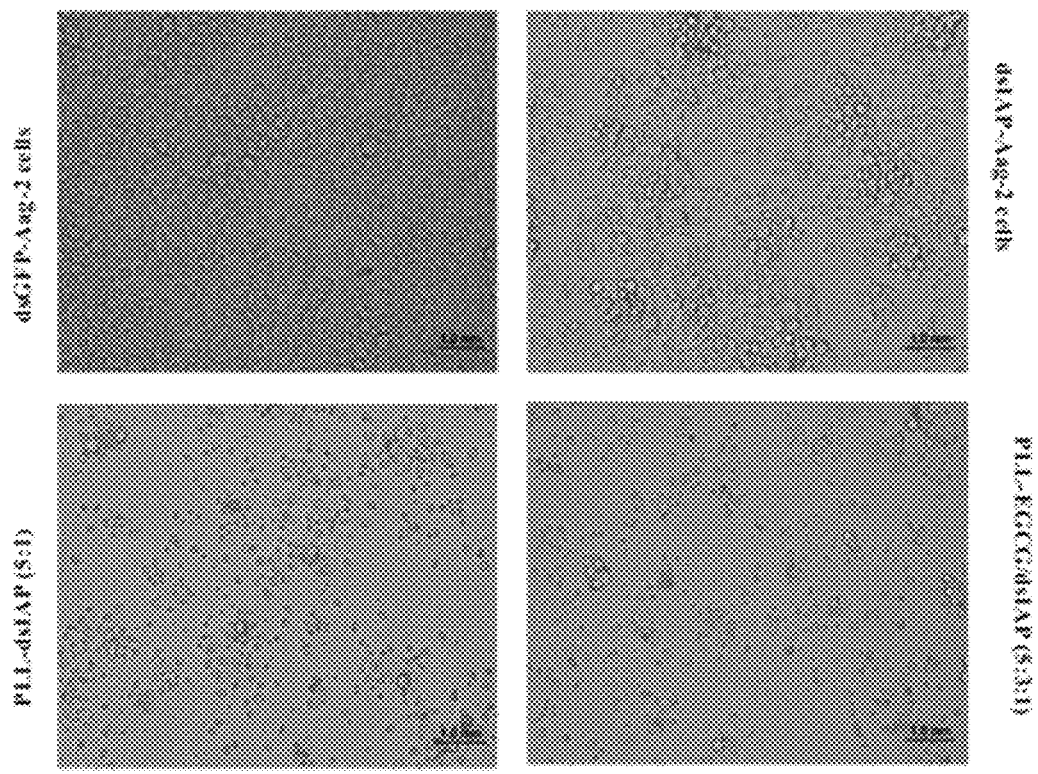
FIG. 16 includes results of a gene knockdown assay of AaIAP gene in Aag-2 cells: Two microgram of naked dsIAP, PLL-dsIAP and dsIAP containing polyplexes delivered into 2×10$^5$ cells. After 72 h mRNA levels was quantified by qRT-PCR. GFP used as a negative control.

In order to determine whether polyplexes can provide effective delivery of dsRNA to Sf9 and Aag-2 insect cells, first the stability of the dsRNA containing polyplexes was evaluated in conditional media from these two cell lines. These two cell lines release nucleases into culture medium which are capable of digesting dsRNAs (unpublished data). The dsRNA in the PLL:EGCG:dsRNA and PLL:dsRNA ployplexes was protected from the digestion by nucleases present in the conditioned medium when compared to naked dsRNA which was digested (FIG. 14). Knockdown efficiency of dsLUC in polyplexes was tested using Sf9 cells stably expressing firefly luciferase gene and did not observe knockdown of dsGFP containing polyplexes and naked dsRNA. In contrast, luciferase dsRNA containing polyplexes exhibited high RNAi efficiencies (68.4% knockdown) compared to PLL-dsRNA nanoparticles (47.6% knockdown) (FIG. 8A). Despite this, successful delivery of dsRNA was facilitated by efficient endosomal escape in cellular system. Intracellular transport of CypHer-5E-labeled dsRNA was studied using a confocal microscope found the accumulation of dsRNA in acidic bodies within Sf9 cells. Greater fluorescence intensity was detected in dsRNA and EGCG-dsRNA. The labeled dsRNA containing polyplexes had much more reduced fluorescence intensity than PLL-dsRNA inside of the cells (FIG. 8B, FIG. 14). Further, the polyplexes uptake efficiency into Sf9 cells was confirmed using Cy-3 labeled dsRNA. The results indicate that polyplexes exhibited higher cellular uptake than PLL-dsRNA. The uptake of PLL-EGCG-dsRNA is much more efficient than naked dsRNA and PLL-dsRNA (FIG. 8C). Moreover, higher intracellular uptake and endosomal escape could dramatically increase cytosolic delivery and gene silencing efficiency. To test the bioactivity of the dsRNA polyplexes, dsIAP polyplexes were exposed to Aag-2 cells and transcript levels were measured relative to a housekeeping gene (S7RP). Polyplexes showed higher gene knockdown efficiency (78%) compared to naked dsRNA and PLL:dsRNA (FIG. 8D, FIG. 16).

Generally, polycations are easily internalized by endocytosis, possibly due to positive charge, amphiphilicity, proton sponge mechanism and high buffering capacity [43, 93-95]. In contrast, EGCG containing polyplexes showed higher cellular uptake and endocytosis in Sf9 insect cells. The uptake of EGCG containing polyplexes is much more efficient than naked dsRNA when endocytosis is mediated via a lipid raft-dependent pathway [84]. These results could possibly be explained by efficient endocytosis and intracellular dsRNA release. These results suggest that EGCG containing polyplexes had greater cellular uptake and decreased lysosomal accumulation, leading to effective silencing of the IAP gene in Aag-2 cells. Polyplexes are not only effective in a mammalian cellular system but also play an important role in their insect cellular system.

Protective Effect of dsRNA in Ex Vivo

Figure 9:
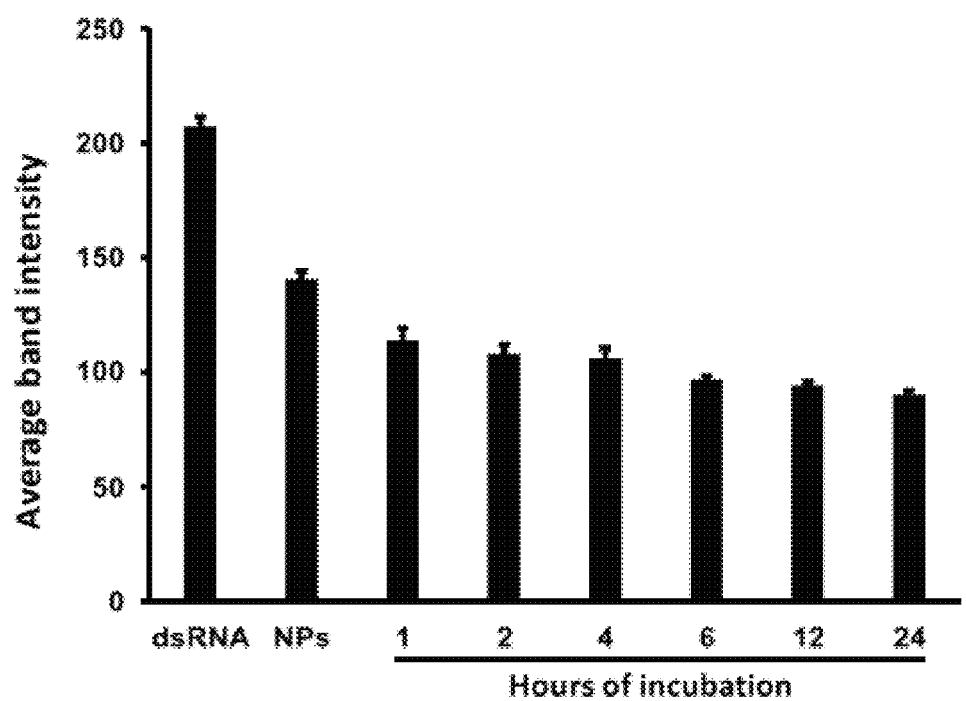
FIG. 9 includes results of a stability assay in mosquito larvae midgut lumen content. PLL-EGCG-dsRNA polyplexes stability assay in midgut lumen content, samples incubated midgut juice at different time intervals (1, 2, 4, 6, 12 and 24 h) samples were collected and stored −20° C. PLL-EGCG-dsRNA polyplexes stability was checked in 1% agarose gel electrophoresis. The gels were stained with GelRed® and photographed under UV light. The band intensity was quantified and Mean±SE (n=3) are shown.
Figure 17:
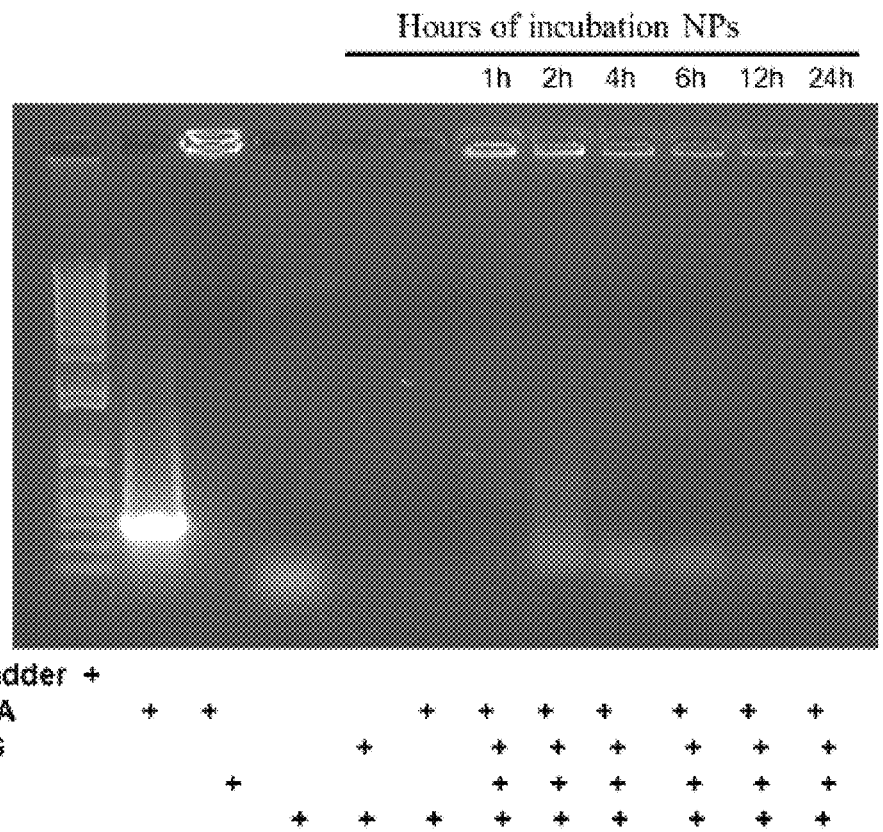
FIG. 17 includes results of PLL-EGCG-dsRNA polyplexes stability assay in mosquito larvae lumen contents. One microgram of dsRNA containing polyplexes exposed one microgram of midgut lumen protein and samples were incubated at different time intervals (1, 2, 4, 6, 12 and 24 h) and stored at −20° C. PLL-EGCG-dsRNA polyplexes stability was checked in 1% agarose gel electrophoresis. The gels were stained with GelRed® and photographed under UV light.

The nucleases present in the lumen content of mosquitoes degraded naked dsRNA within one hour of exposure. In contrast, the PLL-dsRNA nanoparticles protected dsRNA from nuclease degradation (FIG. 9, FIG. 17). However, PLL-EGCG-dsRNA nanoparticles provided stronger protection than PLL-dsRNA in lumen contents. Previous studies reported that EGCG inhibits the activity of nucleases and proteases [71, 84, 90, 96]. This indicates that the protection of dsRNA against nucleases could be achieved with the help of EGCG, which is a requisite for efficient gene delivery in vivo.

In Vivo Characterization of Polyplexes

The effectiveness of gene silencing was further evaluated by testing whether mosquito larvae could be killed when a key developmental gene was targeted using dsRNA delivered by nanoparticles in vivo experiments. Feeding presents additional challenges for the successful delivery of dsRNA, and injection is not a practical approach to control mosquito larvae in the field. Zhang, et al. [20] developed mosquito larvae feeding bioassay and successfully silenced chitin genes. Subsequently, the same approach was applied in *Aedes aegypti* larvae to silence genes [74, 97]. In this study, the same protocol was used to formulate polyplexes that were fed to mosquito larvae.

Figure 10A:
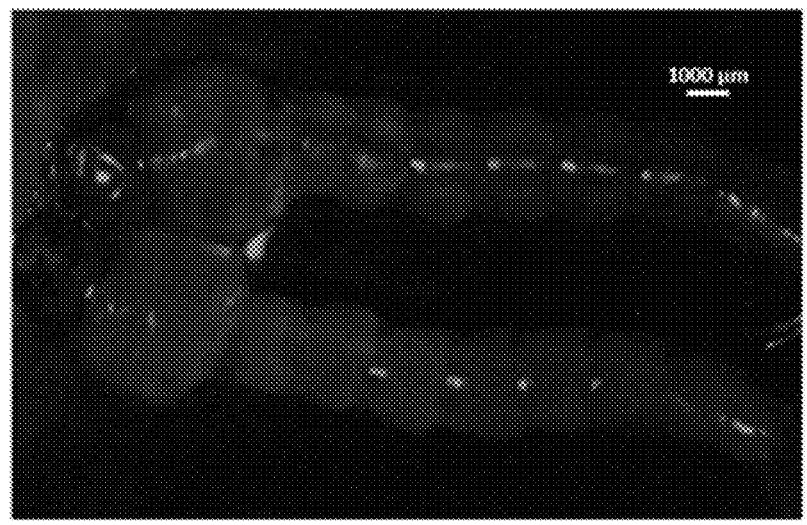
FIGS. 10A-10F includes in vivo characterization of polyplexes.
Figure 10B:
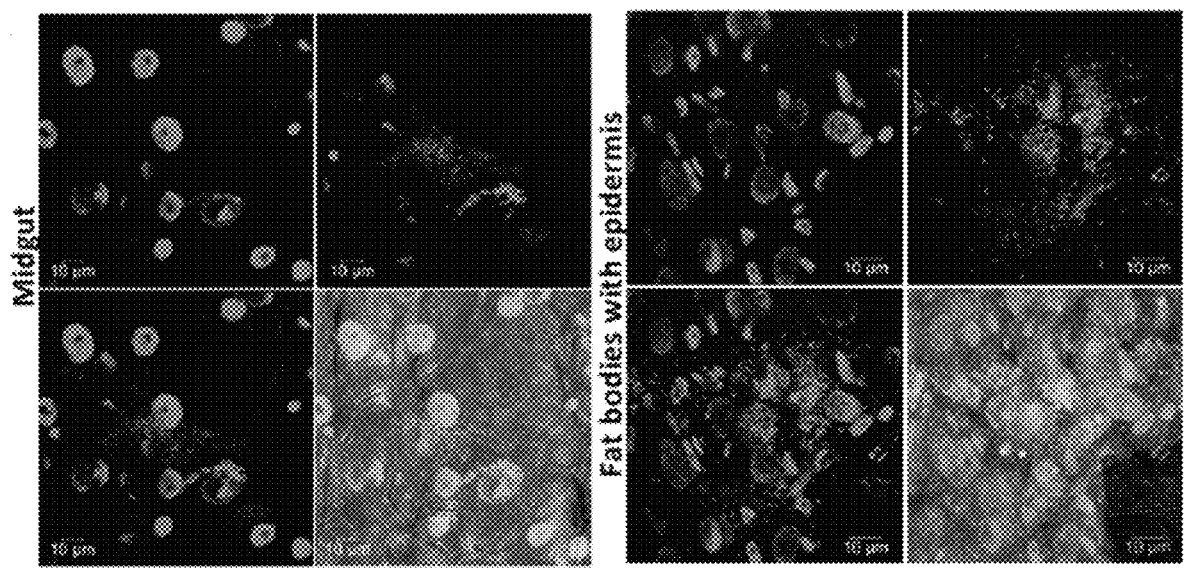
Figure 18:
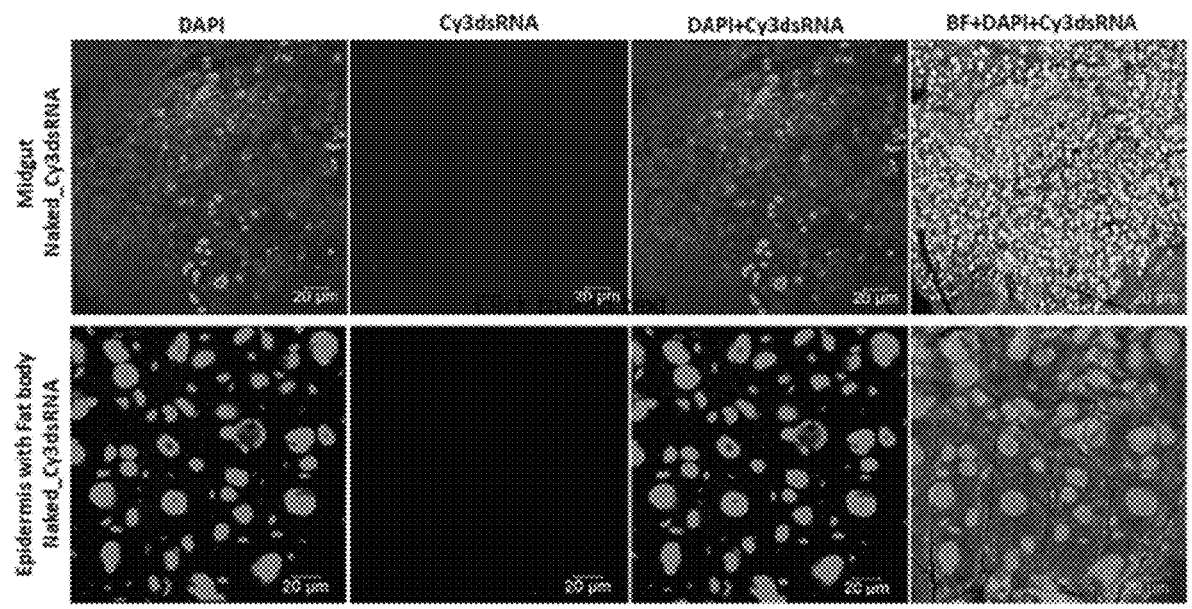
FIG. 18 illustrate that CypHer-5E-labeled dsRNA conjugated to PLL and EGCG nanoparticles reduce the accumulation of dsRNA in the endosomes of Sf9 cells.

First, it was confirmed that the nanoparticles were able to enter gut cells of mosquito larvae by feeding Cy-3 labeled dsRNA polyplexes to mosquito larvae. After larvae had consumed, the polyplexes tissues were examined under fluorescence microscopy. The image shows that red fluorescence was detected throughout the body (FIG. 10A). After larval midgut, fat body with epidermis were dissected and viewed under a confocal microscope. As shown in (FIG. 10B), intense fluorescence signals were detected in the midgut, fat bodies and epidermal cells. Food pellets containing naked Cy-3 dsRNA fed to larvae did not show any signals inside of the cells (FIG. 18), possibly due to nuclease degradation. These results could be explained by possibilities such as size and surface charge of the nanoparticles. Indeed, reports have found that smaller sized nanoparticles facilitate penetration of tissue barriers and entry into cells [98]. Similarly, positively charged nanoparticles are more effective and exhibit faster attachment or internalization in tissues [44, 45, 99, 100].

Figure 10C:
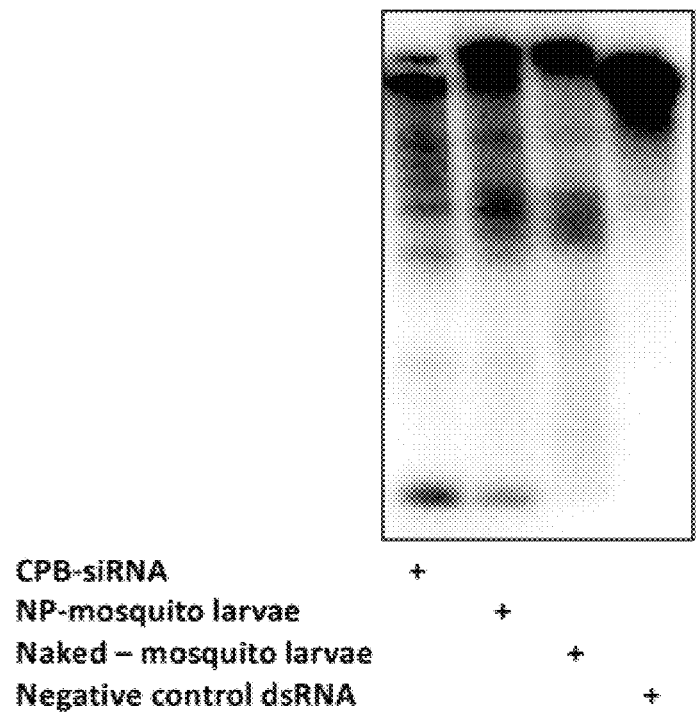

Taken together, delivered polyplexes with smaller size and a positive charge could pass through the peritrophic membrane to be internalized by cells and distributed intracellularly throughout the cytoplasm. In order to determine whether polyplexes facilitate the processing of siRNA in mosquito larvae, a feeding assay was performed using $^{32}$P labeled dsRNA and polyplexes. A positive control sample was prepared by injecting labeled dsRNA into Colorado Potato Beetle (CPB, *Leptinotarsa decemlineata*). In the polyplexes fed to larvae, a siRNA band with good intensity was detected, but no siRNA was detected when larvae were fed naked dsRNA (FIG. 10C). These data confirm that dsRNA containing polyplexes safely transported dsRNA and were processed into siRNA by oral feeding.

Figure 10D:
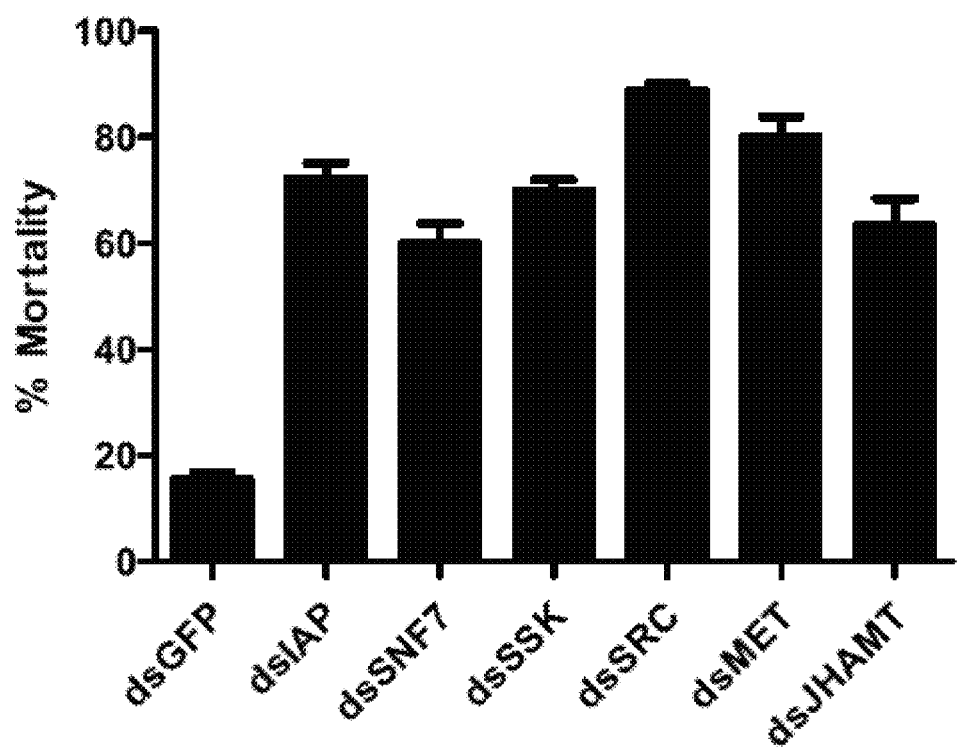
Figure 10E:
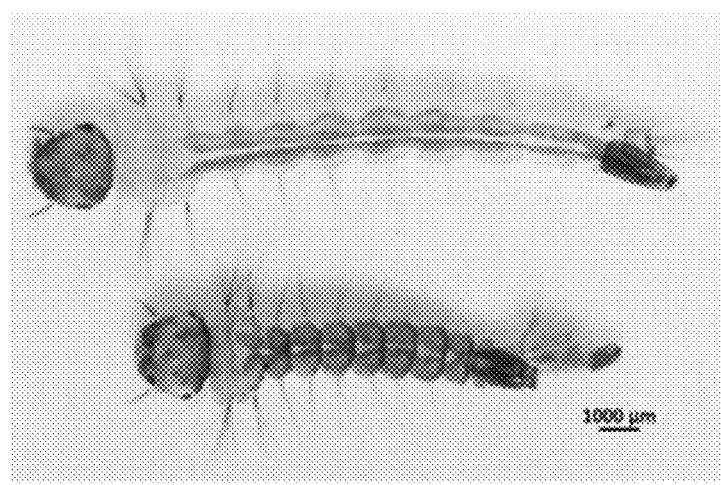
Figure 10F:
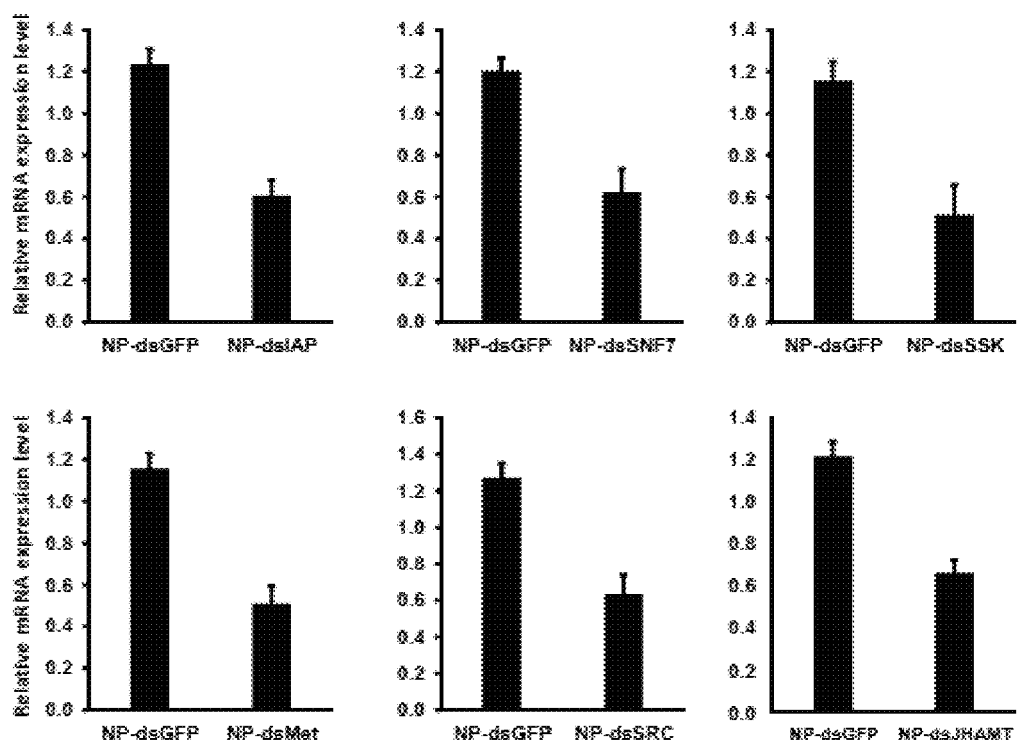

These promising results from the in vivo biodistribution and processing of dsRNA to siRNA lead us to test target genes to knockdown to control mosquito larvae population. Candidate genes were selected based on a previous report [74]. Three midgut genes (IAP, SNF7 and SSK) and three developmental genes (SRC, MET and JHAMT) that play critical roles in the regulation of important physiological functions and larval development were targeted. The corresponding dsRNA targeting these genes was conjugated with polyplexes and fed to mosquito larvae. A conjugated dsRNA targeting green fluorescent protein (GFP) was used as a negative control. Oral administration of polyplexes loaded with dsRNA targeting six genes showed higher mortality (60-90%) than the negative control (15.55%) mortality in mosquito larvae (FIG. 10D). The downregulation of these genes affected larval growth and development and most of treated larvae died before pupation. Additionally, the morphological changes of the MET knockdown larvae exhibited a black color phenotype during the L3 and L4 stages (FIG. 10E). This phenotype could be due to the efficient suppression of MET gene expression. As expected, RT-qPCR analysis of these genes transcript levels confirmed this explanation. The mRNA levels of these genes were clearly reduced after feeding of nanoparticles for 72 h, which demonstrates that all genes were successfully silenced (FIG. 10F). A low-level knockdown (42.21% and 48.0%) and higher mortality (90% and 83.3%) was observed SRC and MET gene compared to other genes, possibly because these two genes are involved in the juvenile hormone and other signaling pathways [101]. The silencing of developmental genes (SRC and MET) leads to severe deficiencies in growth and leading to death.

In conclusion, EGCG-containing polyplexes can stabilize dsRNA delivery into midgut lumen content and efficiently penetrate tissue barrier and enter into cells, resulting in high gene delivery and knockdown efficiency in mosquito larvae. The expression of SRC and MET was efficiently knocked down in fed larvae, leading to death. EGCG containing polyplexes has been reported in mammalian systems but insect model systems to activate RNAi-mediated gene silencing has not been demonstrated. Herein the successful in vitro and in vivo delivery of dsRNA from EGCG containing polyplexes to mosquito larvae is described. The data presented here support that polyplexes produce surprisingly safe and efficient delivery of dsRNA in mosquito larvae.

Figure 19A:
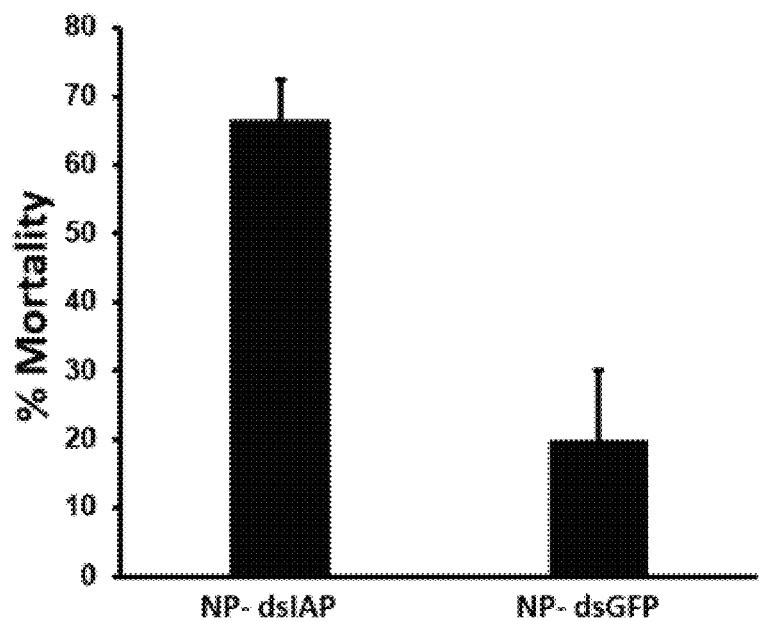
FIGS. 19A-19C include data from an Asian longhorn beetle (ALB) (Coleopteran) larvae PLL-EGCG-dsRNA nanoparticles feeding assay. As shown, PLL-EGCG-dsRNA nanoparticles induced RNAi in ALB larvae. Total 10 µg of dsGFP and dsIAP nanoparticles were mixed with diet and fed to ALB larvae for three days (10 µg/day). The mortality (FIG. 19A) was recorded up to 20 days post feeding. The knockdown of IAP mRNA levels (FIG. 19B) were quantified on 5th day post feeding. Mean±SE (n=3) are shown. Asterisk show statistical difference (P<0.05). The 64.3, 48.9 and 40.5% knockdown of IAP gene expression were observed in the ALB larvae fed on dsIAP nanoparticles. PLL-EGCG-dsRNA nanoparticles also induced RNAi in *spodoptera neonates* by feeding assay. Total 50 µg of dsGFP and dsIAP nanoparticles mixed with 5% sucrose solution and diet were fed neonate *Spodoptera frugiperda*. The mortality rate (FIG. 19C) was recorded up to 10 days of post feeding.
Figure 19B:
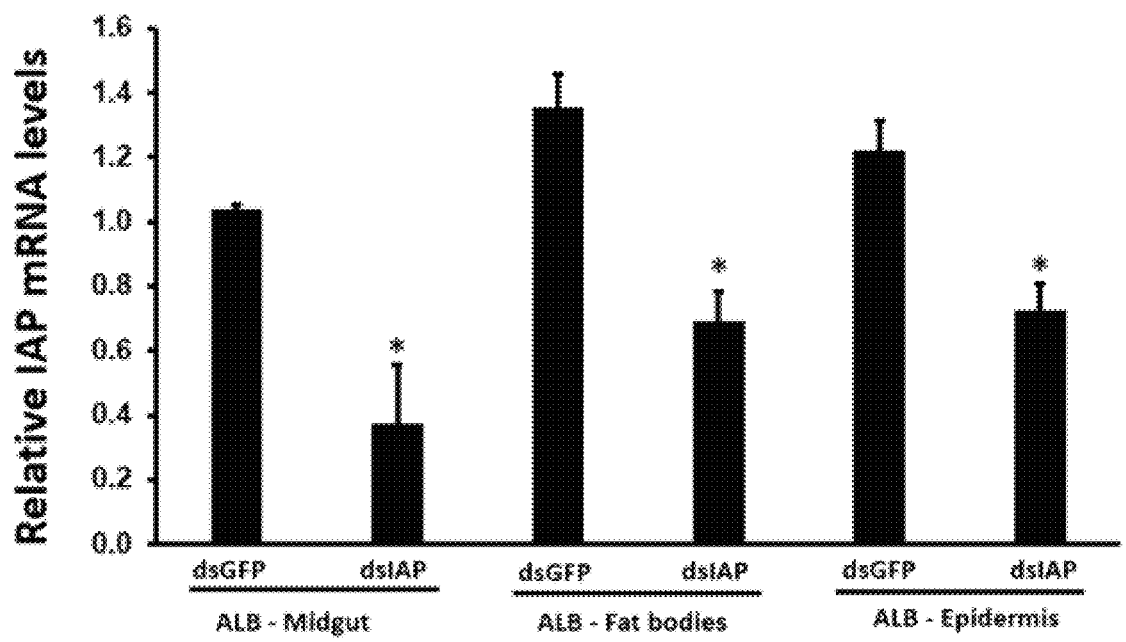
Figure 19C:
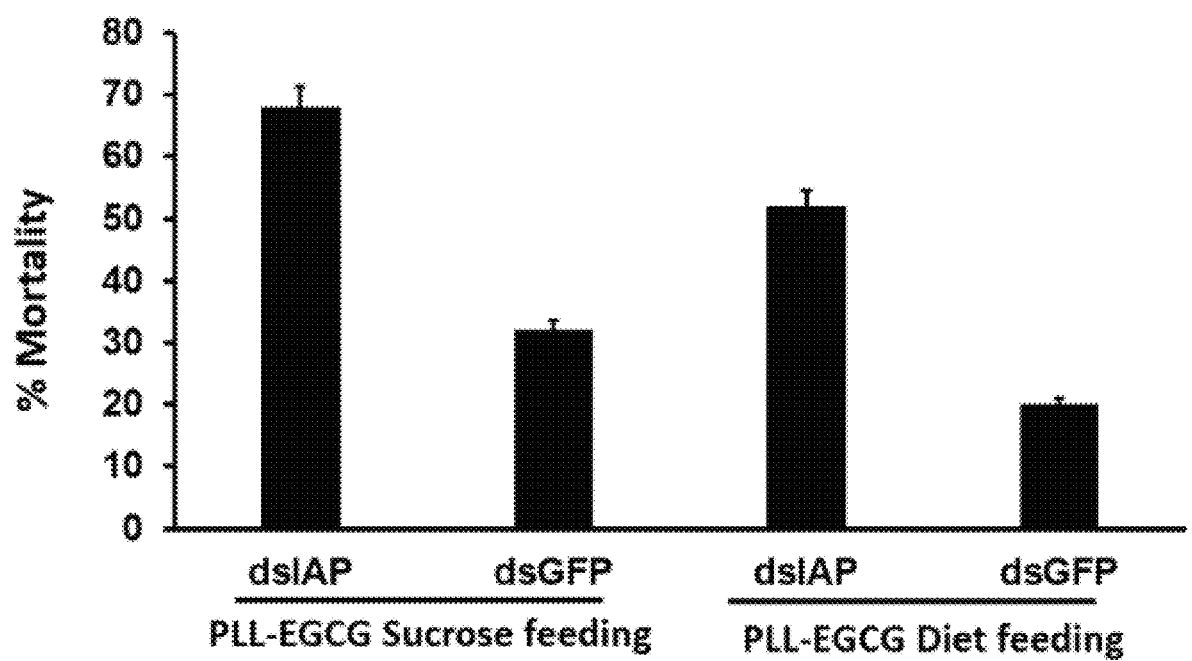

Additional data, from Asian longhorn beetle (ALB), *Anoplophora glabripennis* larvae PLL-EGCG-dsRNA nanoparticles feeding assay, is set forth in FIGS. 19A-19C. With reference to FIGS. 19A and 19B, as shown, PLL-EGCGdsRNA nanoparticles induced RNAi in ALB larvae. Total 10 µg of dsGFP and dsIAP nanoparticles were mixed with diet and fed to ALB larvae for three days (10 µg/day). The mortality was recorded up to 20 days post feeding. The knockdown of IAP mRNA levels were quantified on 5th day post feeding. Mean±SE (n=3) are shown. Asterisk show statistical difference (P<0.05). The 64.3, 48.9 and 40.5% knockdown of IAP gene expression were observed in the ALB larvae fed on dsIAP nanoparticles.

With reference to FIG. 19C, as shown, PLL-EGCG-dsRNA nanoparticles induced RNAi in *Spodoptera* neonates by feeding assay. Total 50 µg of dsGFP and dsIAP nanoparticles mixed with 5% sucrose solution and diet were fed neonate *Spodoptera frugiperda*. The mortality rate was recorded up to 10 days of post feeding.

Preparation and Characterization of PLL:EGCG:dsRNA Polyplexes:

The Natural polyphenol epigallocatechin-3-o-gallate (EGCG) was preincubated with dsRNA prior to mixing with the poly-1-lysine (PLL). The dsRNA was mixed with different amounts of EGCG for 30 min at room temperature. Then the PLL solution was added and vortexed for 10 s, and incubated for 30 min with shaking at 300 rpm at room temperature. The mixer was centrifuged at 13,000 rpm for 10 min, the supernatant was discarded and the pellet was washed three times with deionized water. The polyplexes were analyzed by 1% agarose gel electrophoresis. The size and zeta potential of the prepared polyplexes were determined by dynamic light scattering (Zetasizer Nano ZS90, Malvern). The morphology of polyplexes was determined using transmission electron microscope (TEM).

Complex Formation Assay by Fluorescence Spectroscopy:

The PLL:EGCG:dsRNA complex formation was assayed by fluorescence spectroscopy. One µg of Ethidium Bromide (EB, 20 ng/µl) was mixed with 10 µg of dsRNA in each well of 96-well plates (Thermo Black). Different amounts of (0-100 µg) of EGCG (5 µg/µl) and PLL (10 µg/µl) were then added to each well to form PLL:EGCG:dsRNA polyplexes. After shaking the plate for 10 min at room temperature, fluorescence was measured using the SpectraMaxI3 spectrophotometer (λ excitation=470 nm; λ emission=500-700 nm, Δλ=5 nm).

Determination of dsRNA Loading Efficiency:

To determine the dsRNA loading efficiency of polyplexes, after the formation of the PLL:EGCG:dsRNA polyplexes, free dsRNA in the supernatants was quantified by measuring the absorbance at 260 nm wavelength using UV-vis spectrophotometer. The amount of dsRNA incorporated into the polyplexes was calculated by the difference between the initial quantity of dsRNA (total dsRNA) and the amount of dsRNA in the supernatant (free dsRNA). The supernatant recovered from the polyplexes without dsRNA was used as a blank. Entrapment efficiency was calculated using the following formula; Entrapment efficiency (EE %)=Total dsRNA−Free dsRNA/Total dsRNA×100.

In Vitro Release Studies:

The PLL:EGCG:dsRNA polyplexes were dissolved in 2 ml of aqueous solution in test tubes and incubated at room temperature (25° C.) for 0-72 h. At appropriate time point, (0, 1, 2, 4, 6, 12, 24, 48 and 72 h), the samples were collected and centrifuged at 5000 rpm for 5 min an aliquot of the supernatant was collected and replaced with fresh solution. The amount of dsRNA released from the polyplexes was evaluated using the Nanodrop spectrophotometer. A calibration cure was prepared at each time point using PLL:EGCG polyplexes in order to correct the absorbency due to the PLL:EGCG.

Cell Culture Medium:

Sf9 cells were cultured in Sf-900TM II SFM media (Sigma) and incubated at 27° C. The Sf9-LUC cells were cultured in the same medium except 10 mg/L of Zeocin was added to the medium. Aag2 cells were maintained in Schneider's insect media (Sigma) supplemented with 10% FBS.

Luciferase Assay:

To test the efficiency of nanoparticles, luciferase assay was performed. Sf9 (a cell line developed from *Spodoptera frugiperda*) stable cells expressing the luciferase (Sf9_LUC) gene were seeded in 48-well plates at 0.05×106 cells/well. The cells were exposed to PLL:EGCG:dsLUC nanoparticles. After 3 days, the luciferase activity was measured using a SpectraMax® i3× multi-mode plate reader (Molecular Devices, Sunnyvale, Calif.).

Endosomal Escape Study Using CypHer-5E Labeled dsRNA:

Sf9 cells (1×10$^5$) were seeded into 8-well chamber slides. Twenty ng of CypHer-5E labeled dsGFP prepared as naked dsGFP, EGCG:dsGFP, PLL:dsGFP and PLL:EGCG:dsGFP complexes were mixed with 100 µl fresh SF900II SFM medium and exposed to the cells. At 4 h after adding complexes, the cells were washed twice with 1×PBS and fixed with 4% paraformaldehyde solution for 15 min at RT. The fixed cells were stained with EverBrite™ mounting medium containing DAPI (Biotium, Inc. Fremont, Calif.) and covered with coverslips. The cells were visualized under 63× magnification under a confocal laser scanning microscope (Leica, TCS SP8) using DAPI (for nuclei), Alexa 633 (for CypHer-5E_dsRNA) and bright-field (BF) filters.

Gene Silencing in Aag2 Cells:

For gene silencing study, 6×105 Aag-2 cells were seeded in each well of 6-well culture plates and treated with Nanoparticles-dsIAP or nanoparticles-dsGFP (2 µg). At 72 h after, the cells were harvested and the total RNA was isolated using TRI Reagent (Molecular Research Center Inc., Cincinnati, Ohio) and cDNA was synthesized using M-MLV Reverse Transcriptase (Invitrogen, USA). The cDNA was used as a template for quantitative PCR (qPCR) analysis. Relative expression levels of a target gene were determined using the reference gene, S7RP the 2-ΔΔCT method. Each experiment was repeated at least three times using the samples from independent treatments.

Determination of Stability of Polyplexes Exposed to Lumen Contents:

To investigate the degradation of polyplexes in the lumen of *Ae. aegypti* alimentary canal, alimentary canals were dissected from *Ae. aegypti* larvae, washed and gently crushed in 100 µl of 1×PBS and centrifuged for 10 min at 20,000×g. The supernatant was centrifuged again for 10 min at 20,000×g. Ten microliters of polyplexes containing 1 µg dsRNA were added to 10 µl (1 µg) of lumen contents and the samples were collected at various time points (1, 3, 6, 12 and 24 h). As a control, naked dsRNA was incubated with the lumen contents for 1 h. The samples were resolved on 1.0% (w/v) agarose gel, stained with ethidium bromide and photographed using Alpha Imager™ Gel Imaging System (Alpha Innotech, San Leandro, Calif.) under UV light.

Mosquito Rearing:

*Aedes aegypti* (Waco strain) were reared as described previously. Eggs were collected from lab colony adults and stored dry for approximately 2-4 weeks before hatching. Eggs were hatched in a 64 oz plastic pan containing 300 mL deoxygenated, filtered water inoculated with 10 mL of bovine live powder feeding solution (60 g-L). The pans were maintained in an incubator at 27±1.0° C. under a photoperiodic regime of 16:8 hour (L: D). Freshly molted second-instar larvae were collected and briefly held in a separate pan containing filtered water before being transferred to 24-well plates for bioassays.

dsRNA Synthesis:

Eight candidate genes were selected based on the previous reports on their efficacy as RNAi triggers. The dsRNA targeting these genes was in vitro synthesized using the MEGAscript RNA synthesis kit (Ambion Inc., Foster City, Calif. USA) as described previously (Shukla et al 2016). Briefly, 300-500 bp fragment of each gene was PCR amplified using gene-specific primers containing T7 RNA polymerase sequence at the 5' end. 500 ng of the purified PCR product was used as a template in 20 µL in vitro transcription reaction. The reaction mix was incubated for 16 h at 37° C., followed by 30 min of DNase I treatment. The reaction mixture was heat-inactivated at 70° C. for 10 min and cool down slowly to room temperature. The dsRNA was precipitated by adding 0.1× volume of sodium acetate (3M, pH 5.2) and 2.5× the volumes of 100% ethanol and kept at −20° C. for at least 2 h. The reaction contents were then centrifuged at 4° C. for 15 min. The dsRNA pellet was rinsed with 75% ethanol and centrifuged again at 4° C. for 5 min. The ethanol was removed, and the dsRNA pellet was dried and resuspended in milliQ water. The quality and quantity of dsRNA were checked by agarose gel electrophoresis and NanoDrop-2000 spectrophotometer (Thermo Fisher Scientific Inc., Waltham, Mass.), respectively.

Mosquito Feeding Assay:

Mosquito larval food containing dsRNA polyplexes were prepared as described previously [74]. Briefly, 50 µl of polyplexes containing 50 µg of dsRNA were mixed with 5 mg of bovine liver powder and 1.5% pre-melted agarose gel solution at 55° C. was added to the mixer. A group of 5-7-second instar larvae were transferred to each well of 24-well plate containing 1 ml of deionized water. Each treatment was replicated three times, and each experiment was repeated at least five times. The food pellet containing 50 µg of dsRNA was divided into three equal pieces and distributed to each well. Food containing dsRNA. Mortality was recorded until the control mosquito larvae became adults. The mRNA levels of dsIAP target gene were determined on the $3^{rd}$ day after initiation of the feeding of dsRNA.

Cellular Internalization of Nanoparticles by Confocal Microscopy.

Cy-3 labeled polyplexes were fed to the mosquito larvae, and at 24 h post-feeding, the midgut and epidermis attached with fat body tissues were dissected and washed with 1×PBS buffer. The tissues were fixed with 4% paraformaldehyde solution and incubated at 4° C. overnight under dark conditions. The fixed tissues were mounted on microscope slides stained with EverBrite™ mounting medium containing DAPI (Biotium, Inc. Fremont, Calif.) and examined under 63× magnification in a confocal laser-scanning microscope (Leica TCS SP8) using DAPI, FITC (490-525 wavelength) and bright-field (BF) channels.

dsRNA Processing in Mosquito Larvae.

The $^{32}$P-labelled dsRNA and siRNA were prepared using the protocol described by Shukla et al [102]. Mosquito larvae were starved overnight prior to feeding. Polyplex containing dsRNA about $5\times10^6$ counts per minute (CPM) was mixed with food pellets and fed to mosquito larvae. After three days post-feeding total RNA was isolated from whole larvae and analyzed by 16% Urea-polyacrylamide gel electrophoresis. The gel was dried overnight and the image was analyzed by PhosphorImager.

Quantitative Real-Time PCR (RT-qPCR):

Total RNA was isolated from mosquito larvae using TRIzol reagent (Molecular Research Center Inc., Cincinnati, Ohio) following the manufacturer's protocol. The total RNA was then treated with DNase I (Ambion Inc., Austin, Tex.). Two micrograms of total RNA was used for first-strand cDNA synthesized using M-MLV Reverse Transcriptase (Invitrogen, USA). The first-strand cDNA was used as a template for qPCR analysis. Each qRT-PCR reaction (10 µl final volume) contained 5 µl of Fast Start SYBR Green Master (Roche Diagnostics, Indianapolis), 2 µl of 1:2 diluted cDNA and 0.2 µl each of 10 µM forward and reversed gene-specific primers (Table 1). An initial incubation of 95° C. for 3 min, followed by 40 cycles of 95 for 10 sec, 55 for 20 sec and 72 for 30-sec settings, were used. Each experiment was repeated at least three times using the samples from independent treatments. Relative expression levels of a target gene were determined using the reference gene, S7RP the 2-ΔΔCT method.

Statistical Analysis:

Data are presented as the mean±standard deviation. The statistical significance was determined using an independent sample t-test or one-way analysis of variance (ANOVA). P values of <0.05 were considered significant. The statistical analyses were carried out using SPSS version 12.0 for windows.

Example 3

In this Example, protamine (PS), celfectin (Cf), dsRNA nanoparticles were prepared, characterized, and evaluated for their effectiveness in controlling larvae.

Figure 20:
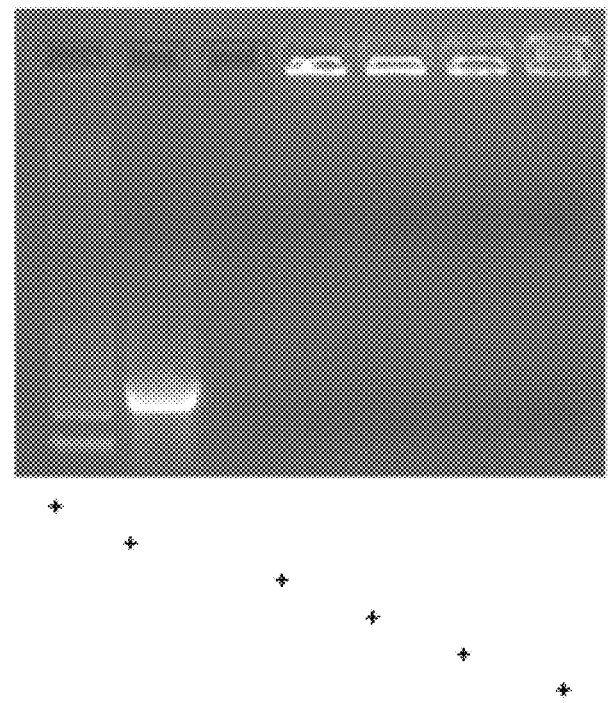
FIG. 20 Protamine:Cellfectin:dsRNA (PS:Cf:dsRNA) polyplexes were prepared with 1 µg dsRNA, 0.1 µg Cf, and varying concentrations of PS (1, 3, 5 and 10 µg) and were evaluated by gel electrophoresis.

PS:Cf:dsRNA polyplexes were prepared with 1 µg dsRNA, 0.1 µg Cf, and varying concentrations of PS (1, 3, 5 and 10 µg). With reference to FIG. 20, the polyplexes were evaluated by gel electrophoresis.

PS:Cf:dsRNA polyplexes produced from different ratios of PS to CF and dsRNA were characterized. Polyplexes size and surface charge was measured using Zetasizer (Malvern). The encapsulation efficiency was calculated from the following equation: Actual dsRNA loaded/theoretical dsRNA loaded×100%. (Table 2).

TABLE 2

Characterization of PS-Cf-dsRNA Polyplexes

| S. No | PS:Cf:dsRNA ratio | Average size (d nm) | Charge (mV) | PDI | Encapsulation efficiency |
| --- | --- | --- | --- | --- | --- |
| 1 | 1:0.1:1 | 142 ± 2.59 | 1.21 ± 0.29 | 0.169 ± 0.05 | 31.48 ± 1.47 |
| 2 | 3:0.1:1 | 113 ± 1.41 | 6.37 ± 0.26 | 0.258 ± 0.016 | 49.76 ± 0.77 |
| 3 | 5:0.1:1 | 91 ± 3.50 | 18.24 ± 0.27 | 0.18 ± 0.007 | 56.68 ± 1.61 |
| 4 | 10:0.1:1 | 68.4 ± 0.122 | 23.1 ± 0.86 | 0.19 ± 0.011 | 75.92 ± 0.76 |

Figure 21:
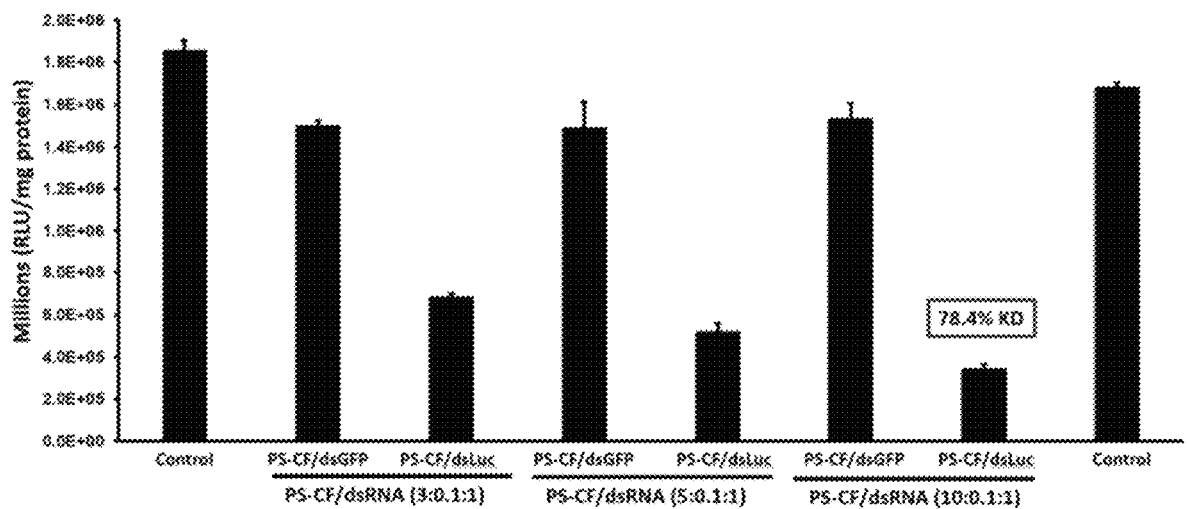
FIG. 21 illustrates functionality of different ratios of PS:Cf:dsRNA nanoparticles using the luciferase activity in Sf9 cells expressing the luciferase gene. The results showed that 78.4% reduced expression of the luciferase gene in the ratio of PS:Cf:dsRNA (10:0.1:1); Asterisk show statistical difference (P<0.05).

The functionality of different ratios of PS:Cf:dsRNA nanoparticles were tested using the luciferase activity in Sf9 cells expressing the luciferase gene. The results showed that 78.4% reduced expression of the luciferase gene in the ratio of PS:Cf:dsRNA (10:0.1:1); Asterisk show statistical difference (P<0.05). (FIG. 21).

Figure 22:
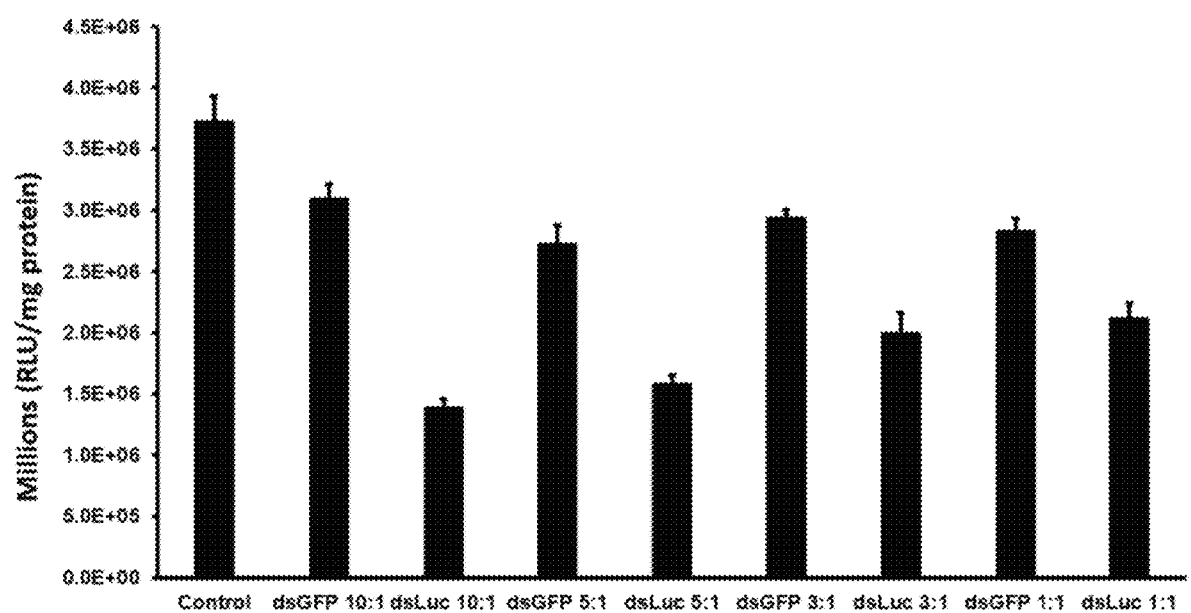
FIG. 22 includes results of testing different ratios of PS-dsRNA nanoparticles using the luciferase activity in Sf9 cells expressing the luciferase gene. The results showed that 45% reduced expression of the luciferase gene in the ratio of PLL-dsRNA (10:1); Asterisk show statistical difference (P<0.05).

Different ratios of PS-dsRNA nanoparticles were tested using the luciferase activity in Sf9 cells expressing the luciferase gene. The results showed that 45% reduced expression of the luciferase gene in the ratio of PLL-dsRNA (10:1); Asterisk show statistical difference (P<0.05). (FIG. 22).

Figure 23A:
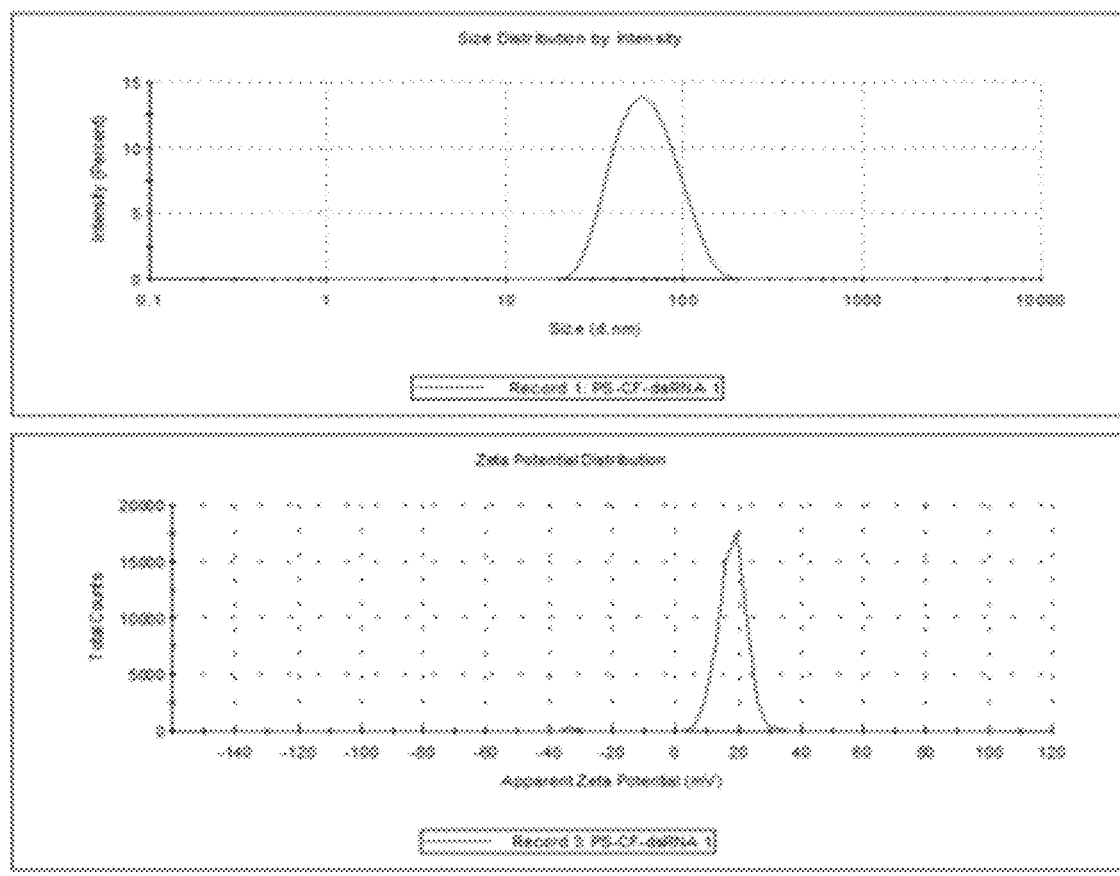
FIGS. 23A and 23B relate to the preparation and characterization of PS:Cf:dsRNA nanoparticles.
Figure 23B:
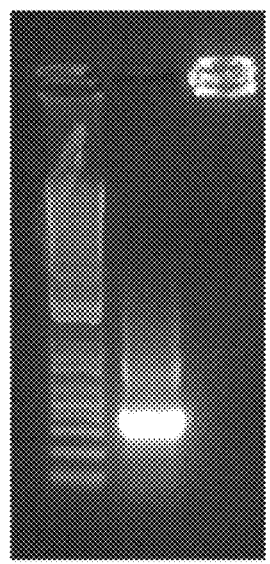

PS:Cf:dsRNA nanoparticles were also characterized. FIG. 23A includes the results of DLS analysis of PS:Cf:dsRNA nanoparticles z-average size and zeta potential. FIG. 23B illustrates the formation of nanoparticles (PS-Cf-dsRNA) as verified using a gel retardation assay.

Figure 24A:
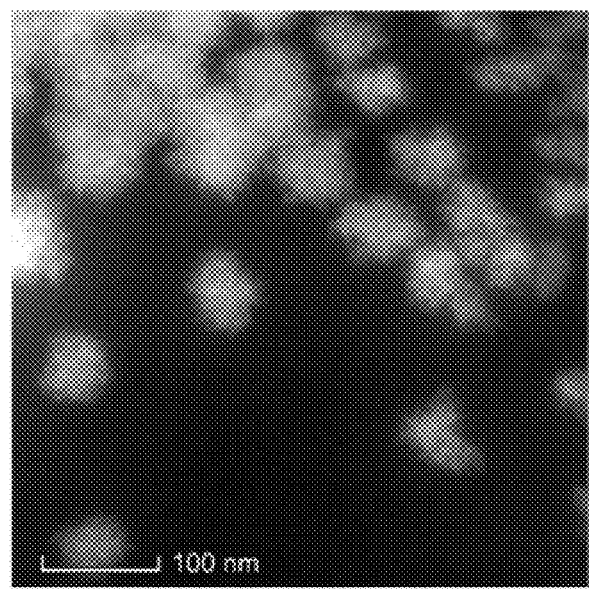
FIG. 24A-24C include transmission electron microscopy (TEM) analysis of PS-Cf-dsRNA nanoparticles.
Figure 24B:
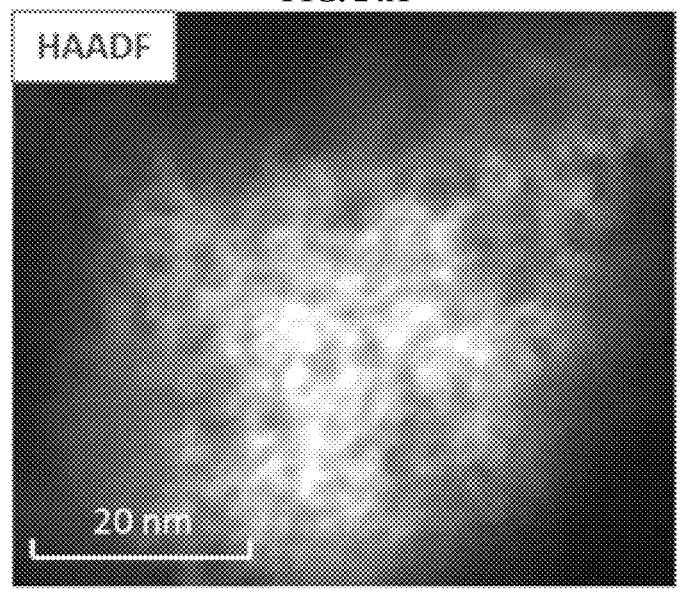
Figure 24C:
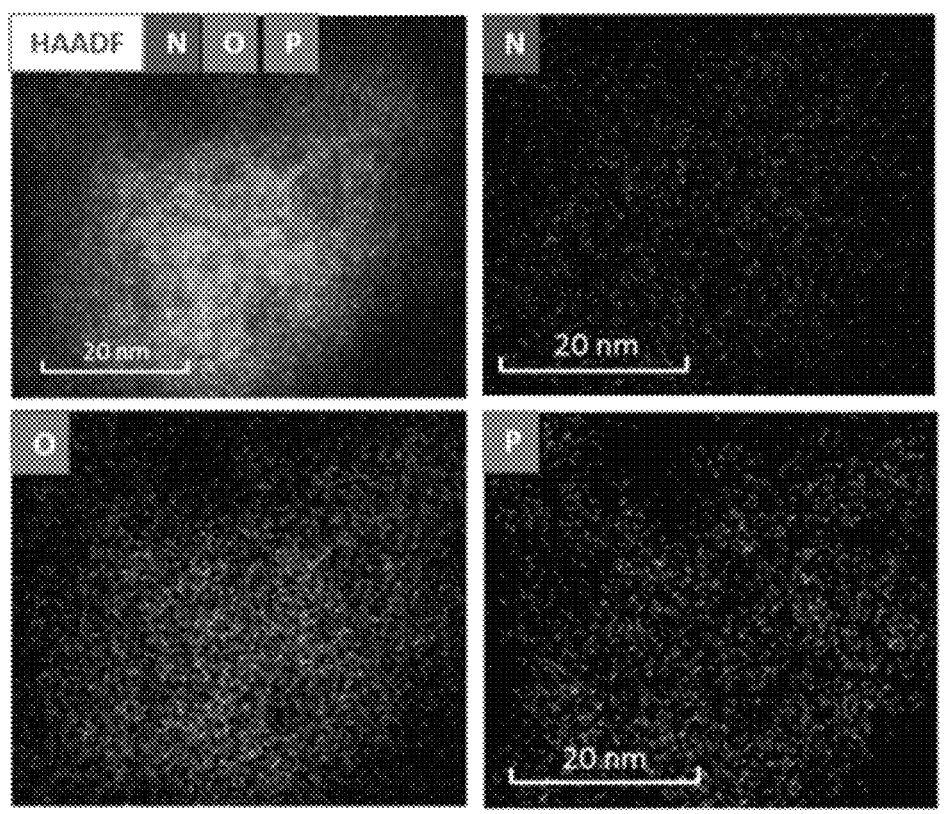

PS-Cf-dsRNA nanoparticles were analyzed using transmission electron microscopy (TEM). FIG. 24A includes morphological characterization of polyplexes in TEM image. FIG. 24B includes higher magnification of single particles in STEM image. FIG. 24C includes elemental analysis of polyplex. (Scale bar=a) 100 nm; b) 10 nm and c) 10 nm).

Figure 25A:
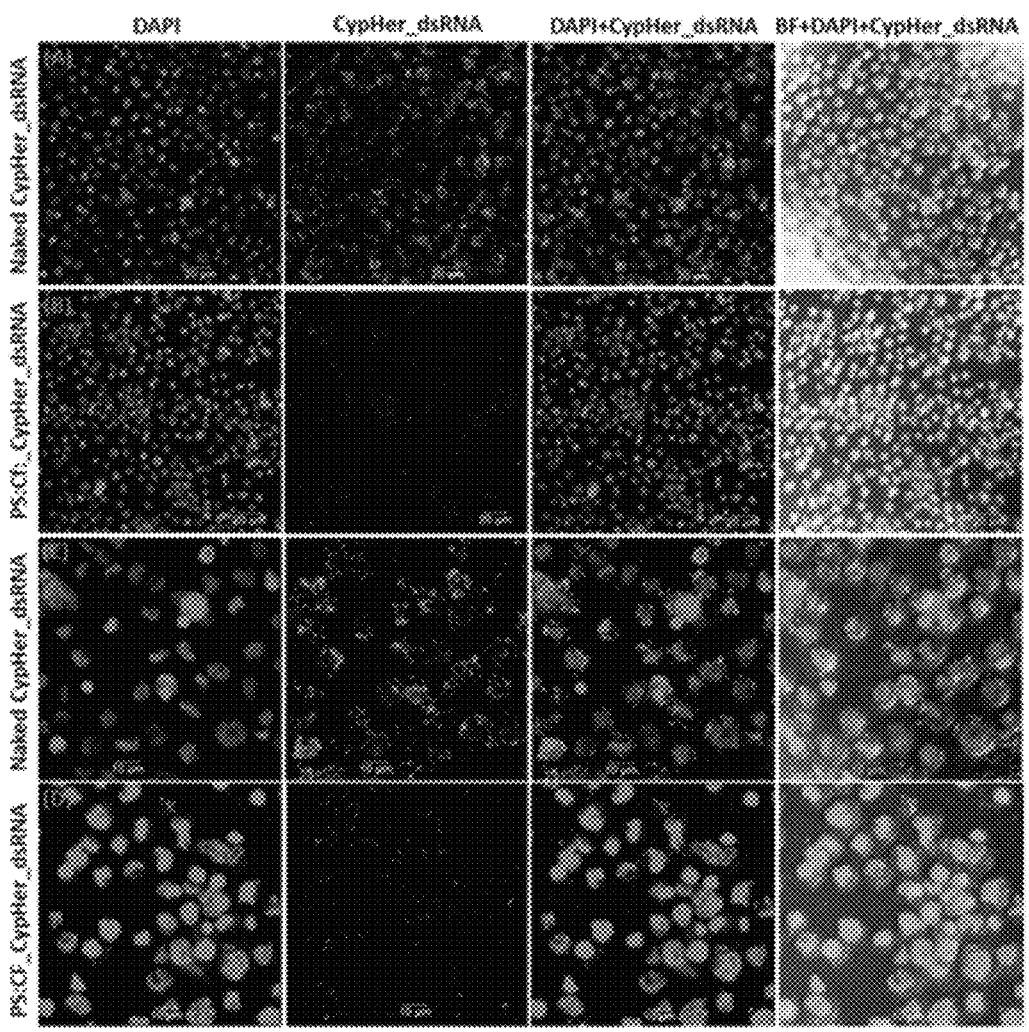
FIGS. 25A and 25B illustrate that CypHer-5E-labeled dsRNA conjugated to Protamine (PS) and cellfectin (Cf) nanoparticles reduce the accumulation of dsRNA in the endosomes of Sf9 cells. 120,000 cells/well were seeded in 8 well chamber slide and incubated 25 ng of naked, conjugated to protamine nanoparticles of CypHer-5E-labeled dsRNA mixed with 100 µl Sf-900 II SFM medium for 4 hr and washed the cells then fixed followed by stained using EverBrite mounting medium with DAPI and visualized the cells under Leica confocal microscope at 63× magnification (scale bar: 20 µm (Rows A-B of FIG. 25A) and 10 µm (Rows C-D of FIG. 25B). dsRNA accumulating bodies were counted in 50 cells and plotted mean number of dsRNA accumulating per cell, as illustrated in FIG. 25B.
Figure 25B:
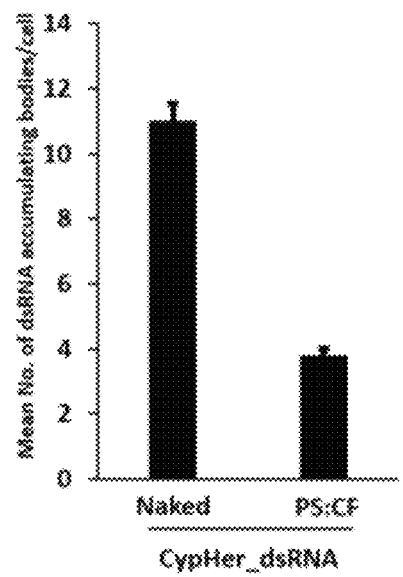

CypHer-5E-labeled dsRNA conjugated to Protamine Sulfate (PS) and celfectin (Cf) nanoparticles were found to reduce the accumulation of dsRNA in the endosomes of Sf9 cells. 120,000 cells/well were seeded in 8 well chamber slide and incubated 25 ng of naked, conjugated to protamine nanoparticles of CypHer-5E-labeled dsRNA mixed with 100 µl Sf-900 II SFM medium for 4 hr and washed the cells then fixed followed by stained using EverBrite mounting medium with DAPI and visualized the cells under Leica confocal microscope at 63× magnification (scale bar: 20 µm (Rows A-B of FIG. 25A) and 10 µm (Rows C-D of FIG. 25B). dsRNA accumulating bodies were counted in 50 cells and plotted mean number of dsRNA accumulating per cell, as illustrated in FIG. 25B.

Figure 26:
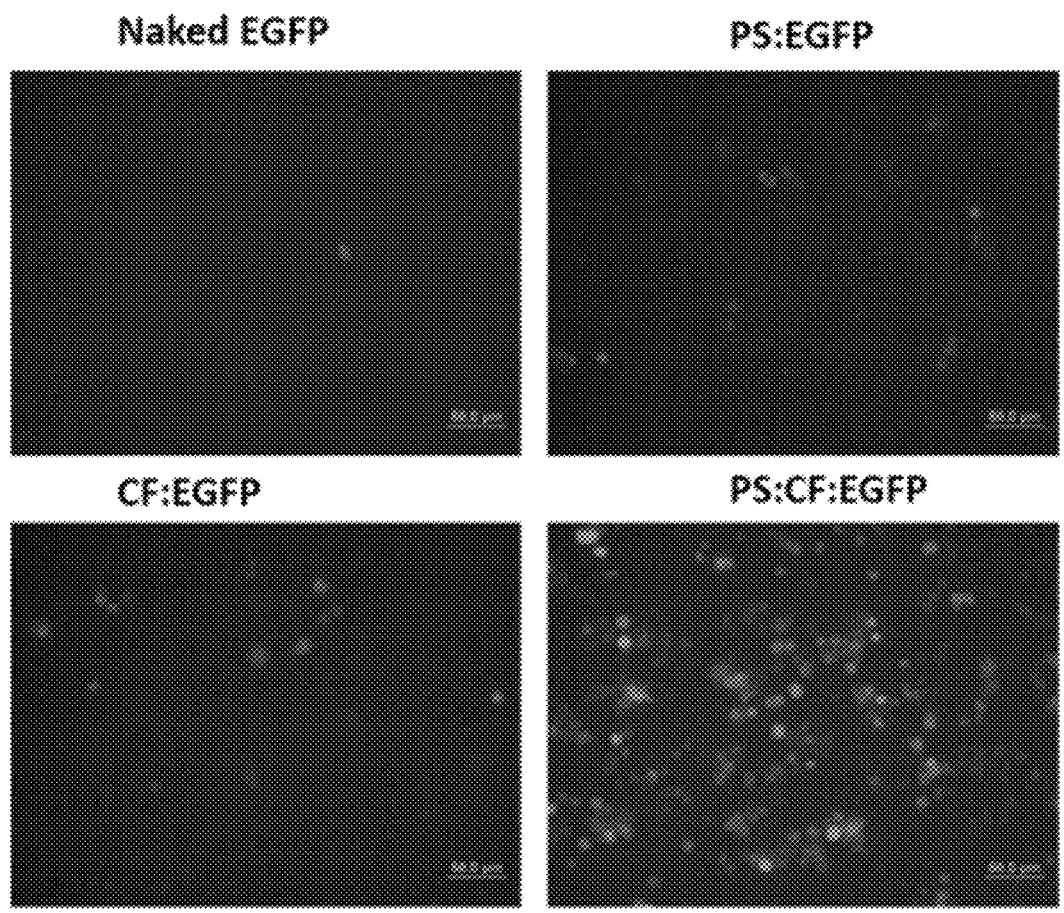
FIG. 26 are fluorescent microscopy images of Sf9 cells transfected by plasmid encoding enhanced green fluorescence protein (EGFP) with different carriers: naked EGFP, PS:EGFP, CF:EGFP, and PS:CF:EGFP. Gene expression was examined after 48 h post transfection.

Fluorescent microscopy images of Sf9 cells transfected by a plasmid encoding enhanced green fluorescent protein (EGFP) with different carriers: naked EGFP, PS:EGFP, CF:EGFP, and PS:CF:EGFP, were obtained (FIG. 26). Gene expression was examined after 48 h post transfection.

Figure 27A:
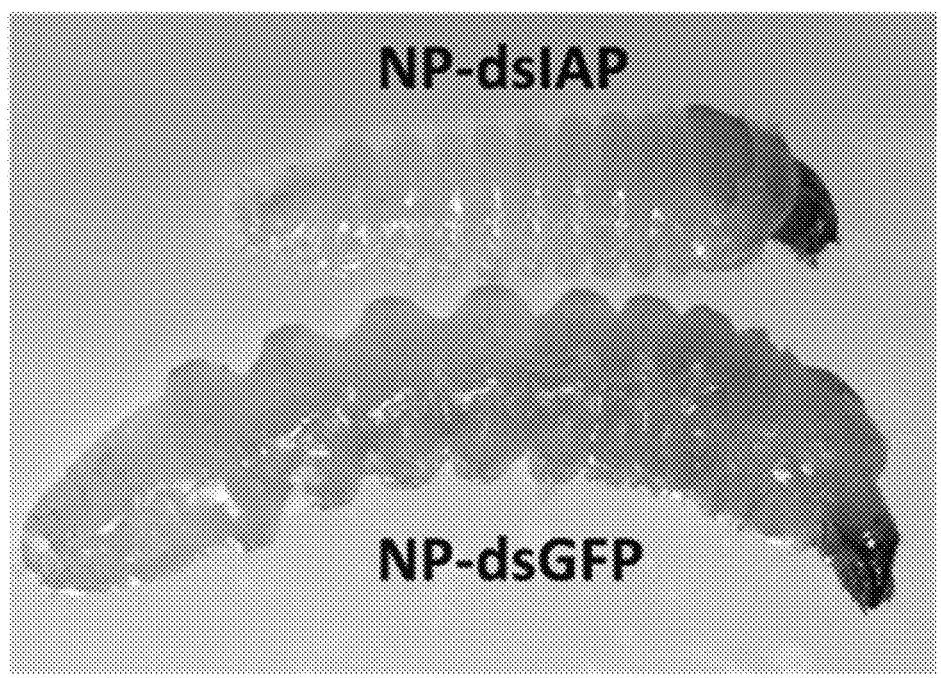
FIG. 27A-27D includes in vivo characterization of PS-Cf-EGFP polyplexes, and shows the results of a sucrose feeding droplet assay of PS/CF-dsRNA nanocomplexes. Nanocomplexes were mixed with 5% sucrose solution and food coloring dye and fed to newly hatched ALB larvae. Polyplexes induced morphological changes in mosquito larvae by feeding (FIG. 27A). The knockdown of IAP gene levels were quantified (FIG. 27B). The mortality was recorded (FIG. 27C). The knockdown of IAP, SNF7, and SSK gene levels were quantified (FIG. 27D).
Figure 27B:
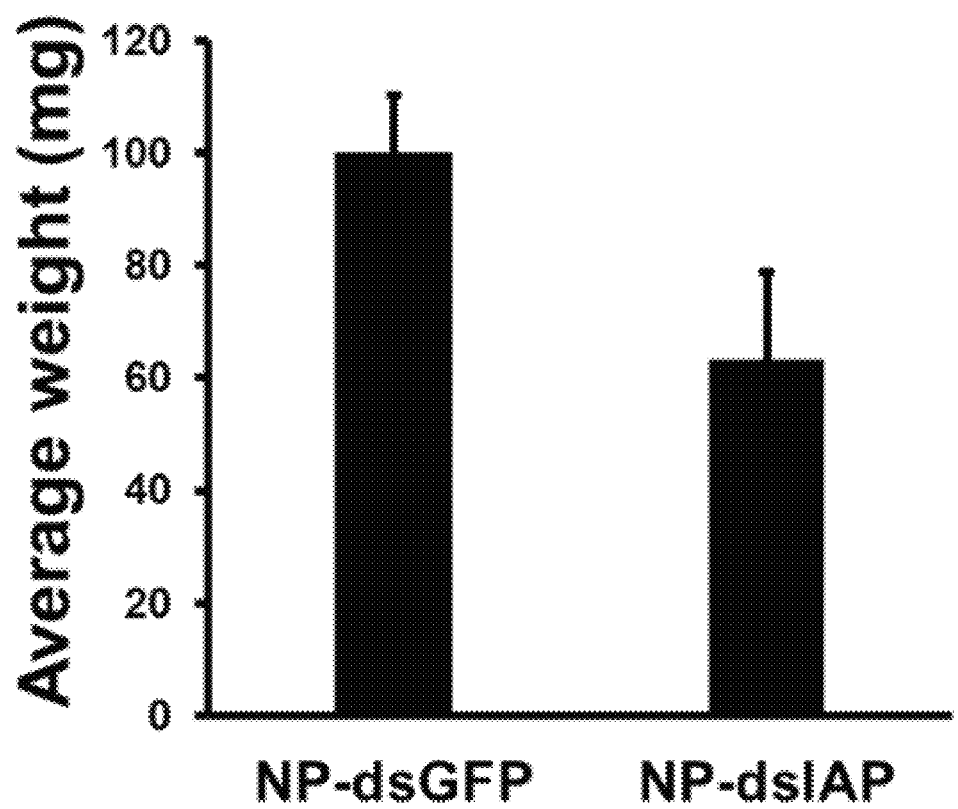
Figure 27C:
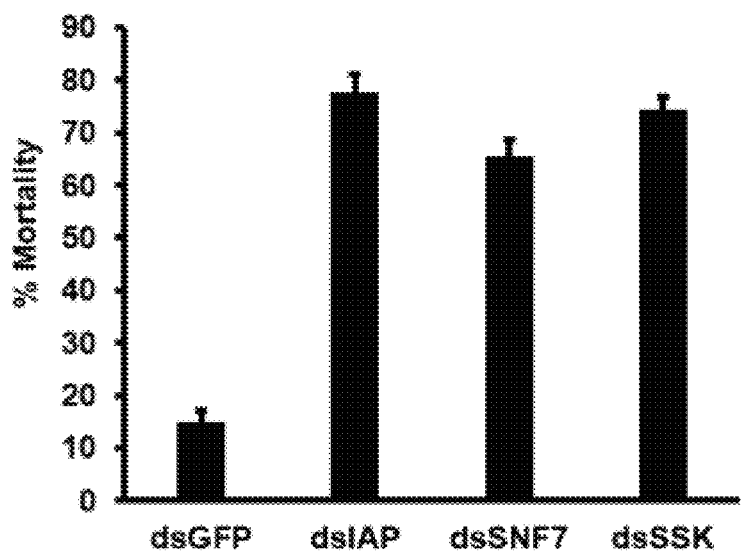
Figure 27D:
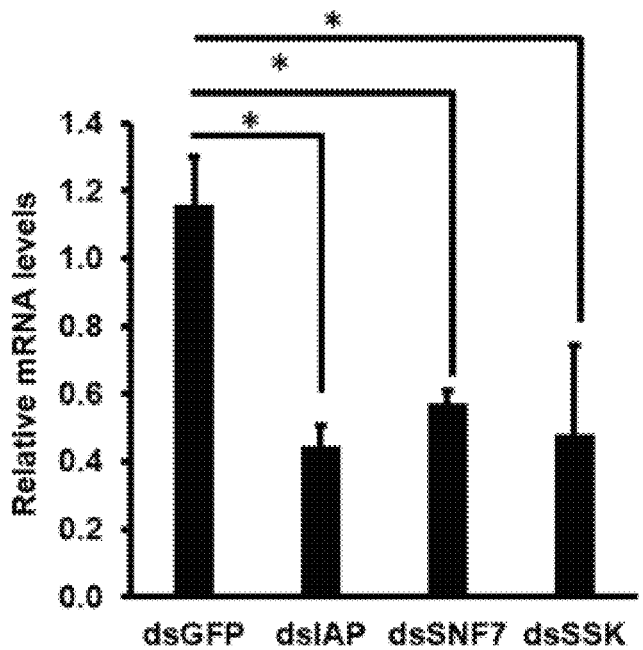

In vivo characterization of polyplexes was conducted using a sucrose feeding droplet assay of PS/CF-dsRNA nanocomplexes. Nanocomplexes were mixed with 5% sucrose solution and food coloring dye and fed to newly hatched ALB larvae. Polyplexes induced morphological changes in mosquito larvae by feeding (FIG. 27A). The knockdown of IAP gene levels were quantified (FIG. 27B). The mortality was recorded (FIG. 27C). The knockdown of IAP, SNF7, and SSK gene levels were quantified (FIG. 27D).

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Liu, N. Insecticide resistance in mosquitoes: impact, mechanisms, and research directions. *Annu Rev Entomol.* 60, 537-559, doi: 10.1146/annurev-ento-010814-020828 (2015).
2. Weetman, D., Mitchell, S. N., Wilding, C. S., Birks, D. P., Yawson, A. E., Essandoh, J., Mawejje, H. D., Djogbenou, L. S., Steen, K., Rippon, E. J. & Clarkson, C. S. Contemporary evolution of resistance at the major insecticide target site gene Ace-1 by mutation and copy number variation in the malaria mosquito *Anopheles gambiae. Mol Ecol.* 24(11), 2656-2672. doi: 10.1111/mec.13197 (2015).
3. Fire, A., Xu, S., Montgomery, M. K., Kostas, S. A., Driver, S. E. & Mello, C C. Potent and specific genetic interference by double-stranded RNA in *Caenorhabditis elegans. Nature.* 391(6669), 806. doi: 10.1038/35888 (1998).
4. Salame, T. M., Ziv, C., Hadar, Y. & Yarden, O. RNAi as a potential tool for biotechnological applications in fungi. *Appl Microbiol Biotechnol.* 89(3), 501-512. doi: 10.1007/s00253-010-2928-1 (2011).
5. Kusaba, M. RNA interference in crop plants. *Curr Opin Biotechnol.* 15(2), 139-143. doi: 10.1016/j.copbio.2004.02.004 (2004).
6. Baum, J. A., Bogaert, T., Clinton, W., Heck, G. R., Feldmann, P., Ilagan, O., Johnson, S., Plaetinck, G., Munyikwa, T., Pleau, M. & Vaughn, T. Control of coleopteran insect pests through RNA interference. *Nat Biotechnol.* 25(11), 1322. doi: 10.1038/nbt1359 (2007).
7. Bumcrot, D., Manoharan, M., Koteliansky, V. & Sah, D. W. RNAi therapeutics: a potential new class of pharmaceutical drugs. *Nat Chem Biol.* 2(12), 711. doi: 10.1038/nchembio839 (2006).
8. Zhu, F., Xu, J., Palli, R., Ferguson, J. & Palli, S. R. Ingested RNA interference for managing the populations of the Colorado potato beetle, *Leptinotarsa decemlineata. Pest Manag Sci.* 67(2), 175-182. doi: 10.1002/ps.2048 (2011).
9. Palli, S. R. RNA interference in Colorado potato beetle: steps toward development of dsRNA as a commercial insecticide. *Curr Opin Insect Sci.* 6, 1-8. doi: 10.1016/j.cois.2014.09.011 (2014).
10. Miller, S. C., Brown, S. J. & Tomoyasu, Y. Larval RNAi in *Drosophila?. Dev Genes Evol.* 218(9), 505-510. doi: 10.1007/s00427-008-0238-8 (2008).
11. Urban-Klein, B., Werth, S., Abuharbeid, S., Czubayko, F. & Aigner, A. RNAi-mediated gene-targeting through systemic application of polyethylenimine (PEI)-complexed siRNA in vivo. *Gene Ther.* 12(5), 461. doi: 10.1038/jg.3302425 (2005).
12. Tomoyasu, Y., Miller, S. C., Tomita, S., Schoppmeier, M., Grossmann, D. & Bucher, G. Exploring systemic RNA interference in insects: a genome-wide survey for RNAi genes in Tribolium. *Genome Biol.* 9(1), R10. doi: 10.1186/gb-2008-9-1-r10 (2008).
13. Garbutt, J. S., Belles, X., Richards, E. H. & Reynolds, S. E. Persistence of double-stranded RNA in insect hemolymph as a potential determiner of RNA interference success: evidence from *Manduca sexta* and *Blattella germanica. J Insect Physiol.* 59(2), 171-178. doi: 10.1016/j.jinsphys.2012.05.013 (2013).
14. Kim, T. H., Kim, S. I., Akaike, T. & Cho, C. S. Synergistic effect of poly (ethylenimine) on the transfection efficiency of galactosylated chitosan/DNA complexes. *J Control Release.* 105(3), 354-366. doi: 10.1016/j.jconre.2005.03.024 (2005).
15. Park, T. G., Jeong, J. H. & Kim, S. W. Current status of polymeric gene delivery systems. *Adv Drug Deliv Rev.* 58(4), 467-486. doi: 10.1016/j.addr.2006.03.007 (2006).
16. Lee, M. K., Chun, S. K., Choi, W. J., Kim, J. K., Choi, S. H., Kim, A., Oungbho, K., Park, J. S., Ahn, W. S. &

Kim, C. K. The use of chitosan as a condensing agent to enhance emulsion-mediated gene transfer. *Biomaterials.* 26(14), 2147-2156. doi: 10.1016/j.biomaterials.2004.07.008 (2005).
17. Shu, X. Z. & Zhu, K. J. The influence of multivalent phosphate structure on the properties of ionically cross-linked chitosan films for controlled drug release. *Eur J Pharm Biopharm.* 54(2), 235-243. doi.org/10.1016/S0939-6411(02)00052-8 (2002).
18. Mao, S., Sun, W. & Kissel, T. Chitosan-based formulations for delivery of DNA and siRNA. *Adv Drug Deliv Rev.* 62(1), 12-27. doi: 10.1016/j.addr.2009.08.004 (2010)
19. Malmo, J., Virum, K. M. & Strand, S. P. Effect of chitosan chain architecture on gene delivery: comparison of self-branched and linear chitosans. *Biomacromolecules.* 12(3), 721-729. doi: 10.1021/bm1013525 (2011).
20. Zhang, X., Zhang, J. & Zhu, K. Y. Chitosan/double-stranded RNA nanoparticle-mediated RNA interference to silence chitin synthase genes through larval feeding in the African malaria mosquito (*Anopheles gambiae*). *Insect Mol Biol.* 19(5), 683-693. doi: 10.1111/j.1365-2583.2010.01029.x(2010).
21. Mysore, K., Flannery, E. M., Tomchaney, M., Severson, D. W. & Duman-Scheel, M. Disruption of *Aedes aegypti* olfactory system development through chitosan/siRNA nanoparticle targeting of semaphorin-1a. *PLoS Negl Trop Dis.* 7(5), 2215. doi: 10.1371/journal.pntd.0002215 (2013).
22. Kumar, D. R., Kumar, P. S., Gandhi, M. R., Al-Dhabi, N. A., Paulraj, M. G. & Ignacimuthu, S., 2016. Delivery of chitosan/dsRNA nanoparticles for silencing of wing development vestigial (vg) gene in *Aedes aegypti* mosquitoes. *Int J Biol Macromol.* 86, 89-95. doi: 10.1016/j.ijbiomac.2016.01.030 (2016).
23. Ko, J. A., Park, H. J., Hwang, S. J., Park, J. B. & Lee, J. S. Preparation and characterization of chitosan microparticles intended for controlled drug delivery. *Int J Pharm.* 249(1-2), 165-174. doi.org/10.1016/S0378-5173(02)00487-8 (2002).
24. Raja, M. A. G., Katas, H. & Wen, T. J. Stability, intracellular delivery, and release of siRNA from chitosan nanoparticles using different cross-linkers. *PLoS One.* 10(6). doi: 10.1371/journal.pone.0128963 (2015).
25. Katas, H. & Alpar, H. O. Development and characterisation of chitosan nanoparticles for siRNA delivery. *J Control Release.* 115(2), 216-225. DOI: 10.1016/j.jconrel.2006.07.021 (2006).
26. Nasti, A., Zaki, N. M., de Leonardis, P., Ungphaiboon, S., Sansongsak, P., Rimoli, M. G. & Tirelli, N. Chitosan/TPP and chitosan/TPP-hyaluronic acid nanoparticles: systematic optimisation of the preparative process and preliminary biological evaluation. *Pharm Res.* 26(8), 1918-1930. DOI: 10.1007/s11095-009-9908-0 (2009).
27. Liu, H. & Gao, C. Preparation and properties of ionically cross-linked chitosan nanoparticles. *Polym. Adv. Technol.* 20(7), 613-619. DOI: 10.1002/pat.1306 (2009).
28. Calvo, P., Remunan-Lopez, C., Vila-Jato, J. L. & Alonso, M. J., 1997. Novel hydrophilic chitosan-polyethylene oxide nanoparticles as protein carriers. *J. Appl. Polym. Sci.* 63(1), 125-132. doi.org/10.1002/(SICI)1097-4628(19970103)63:1<125::AID-APP13>3.0.CO; 2-4 (1997).
29. Hu, B., Pan, C., Sun, Y., Hou, Z., Ye, H., Hu, B. & Zeng, X. Optimization of fabrication parameters to produce chitosan-tripolyphosphate nanoparticles for delivery of tea catechins. *J Agric Food Chem.* 56(16), 7451-7458. doi: 10.1021/jf801111c (2008).
30. Harris, R., Lecumberri, E., Mateos-Aparicio, I., Mengibar, M. & Heras, A. Chitosan nanoparticles and microspheres for the encapsulation of natural antioxidants extracted from *Ilex paraguariensis*. *Carbohydr Polym.* 84(2), 803-806. doi.or 10.1016/j.carbpol.2010.07.003 (2011).
31. Gan, Q. & Wang, T. Chitosan nanoparticle as protein delivery carrier—systematic examination of fabrication conditions for efficient loading and release. *Colloids Surf B Biointerfaces.* 59(1), 24-34. doi: 10.1016/j.colsurfb.2007.04.009 (2007).
32. Sun, Y. & Wan, A. Preparation of nanoparticles composed of chitosan and its derivatives as delivery systems for macromolecules. *J. Appl. Polym. Sci.* 105(2), 552-561 (2007).
33. Lin, Y. H., Mi, F. L., Chen, C. T., Chang, W. C., Peng, S. F., Liang, H. F. & Sung, H. W. Preparation and characterization of nanoparticles shelled with chitosan for oral insulin delivery. *Biomacromolecules.* 8(1), 146-152. doi: 10.1021/bm0607776 (2007).
34. Raj, L. F. A. A., Jonisha, R., Revathi, B. & Jayalakshmy, E. Preparation and characterization of BSA and chitosan nanoparticces for sustainable delivery system for quercetin. *J Appl. Pharm. Sci.* 5, 1-5 (2015).
35. Grenha, A., Seijo, B. & Remuñán-López, C. Microencapsulated chitosan nanoparticles for lung protein delivery. *Eur J Pharm Sci.* 25(4-5), 427-437. doi: 10.1016/j.ejps.2005.04.009 (2005).
36. Janes, K. A., Calvo, P. & Alonso, M. J. Polysaccharide colloidal particles as delivery systems for macromolecules. *Adv Drug Deliv Rev.* 47(1), 83-97. doi.org/10.1016/S0169-409X(00)00123-X (2001).
37. Howard, K. A. Delivery of RNA interference therapeutics using polycation-based nanoparticles. *Adv Drug Deliv Rev.* 61(9), 710-720. doi: 10.1016/j.addr.2009.04.001 (2009).
38. Panyam, J. & Labhasetwar, V. Biodegradable nanoparticles for drug and gene delivery to cells and tissue. *Adv Drug Deliv Rev.* 55(3), 329-347. doi.org/10.1016/S0169-409X(02)00228-4 (2003).
39. Vandenberg, G. W., Drolet, C., Scott, S. L. & De la Noüe, J. Factors affecting protein release from alginate-chitosan coacervate microcapsules during production and gastric/intestinal simulation. *J Control Release.* 77(3), 297-307. doi.org/10.1016/S0168-3659(01)00517-X (2001).
40. Papadimitriou, S. A., Achilias, D. S. & Bikiaris, D. N. Chitosan-g-PEG nanoparticles ionically crosslinked with poly (glutamic acid) and tripolyphosphate as protein delivery systems. *Int J Pharm.* 430(1-2), 318-327. doi: 10.1016/j.ijpharm.2012.04.004 (2012).
41. Ahmad Nor, Y., Niu, Y., Karmakar, S., Zhou, L., Xu, C., Zhang, J., Zhang, H., Yu, M., Mahony, D., Mitter, N. & Cooper, M. A. Shaping nanoparticles with hydrophilic compositions and hydrophobic properties as nanocarriers for antibiotic delivery. *ACS Cent Sci.* 1(6), 328-334. doi: 10.1021/acscentsci.5b00199 (2015).
42. Rampino, A., Borgogna, M., Blasi, P., Bellich, B. & Cesàro, A. Chitosan nanoparticles: preparation, size evolution and stability. *Int J Pharm.* 455(1-2), 219-228. doi: 10.1016/j.ijpharm.2013.07.034 (2013).
43. Sonawane, N. D., Szoka, F. C. & Verkman, A. S. Chloride accumulation and swelling in endosomes enhances DNA transfer by polyamine-DNA polyplexes. *J Biol Chem.* 278(45), 44826-44831. doi: 10.1074/jbc.M308643200 (2003).
44. Phanse, Y., Dunphy, B. M., Perry, J. L., Airs, P. M., Paquette, C. C., Carlson, J. O., Xu, J., Luft, J. C., DeSimone, J. M., Beaty, B. J. & Bartholomay, L. C. Biodistribution and toxicity studies of print hydrogel nanoparticles in mosquito larvae and cells. *PLoS Negl Trop Dis.* 9(5). doi: 10.1371/journal.pntd.0003735 (2005).

45. Paquette, C. C., Phanse, Y., Perry, J. L., Sanchez-Vargas, I., Airs, P. M., Dunphy, B. M., Xu, J., Carlson, J. O., Luft, J. C., DeSimone, J. M. & Bartholomay, L. C. Biodistribution and trafficking of hydrogel nanoparticles in adult mosquitoes. PLoS Negl Trop Dis. 9(5). doi: 10.1371/journal.pntd.0003745 (2015).

46. Wischke, C., Borchert, H. H., Zimmermann, J., Siebenbrodt, I. and Lorenzen, D. R. Stable cationic microparticles for enhanced model antigen delivery to dendritic cells. *J Control Release.* 114(3), 359-368. doi: 10.1016/j.jconrel.2006.06.020 (2006).

47. Huang, Q., Deveraux, Q. L., Maeda, S., Stennicke, H. R., Hammock, B. D. & Reed, J. C. Cloning and characterization of an inhibitor of apoptosis protein (IAP) from *Bombyx mori. Biochim Biophys Acta.* 1499(3), 191-198. doi.org/10.1016/50167-4889(00)00105-1(2001).

48. Wang, H. & Clem, R. J. The role of IAP antagonist proteins in the core apoptosis pathway of the mosquito disease vector *Aedes aegypti. Apoptosis.* 16(3), 235-248. doi: 10.1007/s10495-011-0575-3 (2011).

49. Puglise, J. M., Estep, A. S. & Becnel, J. J. Expression profiles and RNAi silencing of Inhibitor of Apoptosis transcripts in *Aedes, Anopheles*, and *Culex* mosquitoes (Diptera: Culicidae). *J Med Entomol.* 53(2), 304-314. doi: 10.1093/jme/tjv191 (2015).

50. Walker III, W. B. & Allen, M. L. RNA interference-mediated knockdown of IAP in *Lygus lineolaris* induces mortality in adult and pre-adult life stages. *Entomol. Exp. Appl.* 138(2), 83-92. doi: 10.1111/j.1570-7458.2010.01078.x (2011).

51. Mogilicherla, K., Howell, J. L. & Palli, S. R. Improving RNAi in the Brown Marmorated Stink Bug: Identification of target genes and reference genes for RT-qPCR. *Sci Rep.* 8(1), 3720. doi: 10.1038/s41598-018-22035-z (2018).

52. Rodrigues, T. B., Dhandapani, R. K., Duan, J. J. & Palli, S. R. RNA interference in the Asian Longhorned Beetle: Identification of Key RNAi Genes and Reference Genes for R T-qPCR. *Sci Rep.* 7(1), 8913. doi: 10.1038/s41598-017-08813-1 (2017).

53. Rodrigues, T. B., Rieske, L. K., Duan, J., Mogilicherla, K. & Palli, S. R. Development of RNAi method for screening candidate genes to control emerald ash borer, *Agrilus planipennis. Sci Rep.* 7(1), 7379. doi: 10.1038/s41598-017-07605-x (2017).

54. Das, S., Debnath, N., Cui, Y., Unrine, J. & Palli, S. R. Chitosan, carbon quantum dot, and silica nanoparticle mediated dsRNA delivery for gene silencing in *Aedes aegypti*: a comparative analysis. *ACS Appl Mater Interfaces.* 7(35), 19530-19535. doi: 10.1021/acsami.5b05232 (2015).

55. Shu, S., Sun, C., Zhang, X., Wu, Z., Wang, Z. & Li, C. Hollow and degradable polyelectrolyte nanocapsules for protein drug delivery. *Acta Biomater.* 6(1), 210-217. doi.org/10.1016/j.actbio.2009.06.020 (2010)

56. Shukla, J. N., Kalsi, M., Sethi, A., Narva, K. E., Fishilevich, E., Singh, S., Mogilicherla, K. & Palli, S. R. Reduced stability and intracellular transport of dsRNA contribute to poor RNAi response in lepidopteran insects. *RNA Biol.* 13(7), 656-669. doi: 10.1080/15476286.2016.1191728 (2016).

57. Ge, Y., Zhang, Y., He, S., Nie, F., Teng, G. and Gu, N. Fluorescence modified chitosan-coated magnetic nanoparticles for high-efficient cellular imaging. *Nanoscale Res Lett.* 4(4), 287. doi: 10.1007/s11671-008-9239-9 (2009).

58. Bai, H., Ramaseshadri, P. & Palli, S. R. Identification and characterization of juvenile hormone esterase gene from the yellow fever mosquito, *Aedes aegypti. Insect Biochem Mol Biol.* 37(8), 829-837. doi: 10.1016/j.ibmb.2007.05.010 (2007).

59. Hu, X., Richtman, N. M., Zhao, J. Z., Duncan, K. E., Niu, X., Procyk, L. A., Oneal, M. A., Kernodle, B. M., Steimel, J. P., Crane, V. C. & Sandahl, G. Discovery of midgut genes for the RNA interference control of corn rootworm. *Sci Rep.* 6, 30542. doi: 10.1038/srep30542 (2016).

60. Mysore, K., Hapairai, L. K., Sun, L., Harper, E. I., Chen, Y., Eggleson, K. K., Realey, J. S., Scheel, N. D., Severson, D. W., Wei, N. & Duman-Scheel, M. Yeast interfering RNA larvicides targeting neural genes induce high rates of *Anopheles* larval mortality. *Malar J.* 16(1), 461. doi: 10.1186/s12936-017-2112-5 (2017).

61. Zhu, K. Y. and S. R. Palli, Mechanisms, Applications, and Challenges of Insect RNA Interference. Annu Rev Entomol, 2020. 65: p. 293-311.

62. Wynant, N., D. Santos, and J. Vanden Broeck, *Biological mechanisms determining the success of RNA interference in insects.* Int Rev Cell Mol Biol, 2014. 312: p. 139-67.

56. Shukla, J. N., et al., *Reduced stability and intracellular transport of dsRNA contribute to poor RNAi response in lepidopteran insects.* RNA Biol, 2016. 13(7): p. 656-69.

63. Singh, I. K., et al., *Comparative analysis of double-stranded RNA degradation and processing in insects.* Sci Rep, 2017. 7(1): p. 17059.

64. Christiaens, O., L. Swevers, and G. Smagghe, *DsRNA degradation in the pea aphid (Acyrthosiphon pisum) associated with lack of response in RNAi feeding and injection assay.* Peptides, 2014. 53: p. 307-14.

65. Yoon, J. S., D. Gurusamy, and S. R. Palli, *Accumulation of dsRNA in endosomes contributes to inefficient RNA interference in the fall armyworm, Spodoptera frugiperda.* Insect Biochem Mol Biol, 2017. 90: p. 53-60.

66. Spit, J., et al., *Knockdown of nuclease activity in the gut enhances RNAi efficiency in the Colorado potato beetle, Leptinotarsa decemlineata, but not in the desert locust, Schistocerca gregaria.* Insect Biochem Mol Biol, 2017. 81: p. 103-116.

67. Song, H., et al., *A double-stranded RNA degrading enzyme reduces the efficiency of oral RNA interference in migratory locust.* Insect Biochem Mol Biol, 2017. 86: p. 68-80.

68. Peng, Y., et al., *Identification and characterization of multiple dsRNases from a lepidopteran insect, the tobacco cutworm, Spodoptera litura (Lepidoptera: Noctuidae).* Pestic Biochem Physiol, 2020. 162: p. 86-95.

69. He, B., et al., *Fluorescent nanoparticle delivered dsRNA toward genetic control of insect pests.* Adv Mater, 2013. 25(33): p. 4580-4.

70. Christiaens, O., et al., *Increased RNAi Efficacy in Spodoptera exigua via the Formulation of dsRNA With Guanylated Polymers.* Front Physiol, 2018. 9: p. 316.

71. Liang, K., et al., *Self-assembled ternary complexes stabilized with hyaluronic acid-green tea catechin conjugates for targeted gene delivery.* J Control Release, 2016. 226: p. 205-16.

72. Mitter, N., et al., *Clay nanosheets for topical delivery of RNAi for sustained protection against plant viruses.* Nat Plants, 2017. 3: p. 16207.

73. Sajeesh, S., et al., *Long dsRNA-mediated RNA interference and immunostimulation: a targeted delivery approach using polyethyleneimine based nano-carriers.* Mol Pharm, 2014. 11(3): p. 872-84.
74. Dhandapani, R. K., et al., *Development of CS-TPP-dsRNA nanoparticles to enhance RNAi efficiency in the yellow fever mosquito, Aedes aegypti.* Sci Rep, 2019. 9(1): p. 8775.
75. Dahlman, J., et al., *In vivo endothelial siRNA delivery using polymeric nanoparticles with low molecular weight.* Nat Nanotechnol, 2014. 9(8): p. 648-655.
76. Zhao, Y., et al., *PolyMetformin combines carrier and anticancer activities for in vivo siRNA delivery.* Nat Commun, 2016. 7: p. 11822.
77. Cui, J., et al., *Ex vivo pretreatment of human vessels with siRNA nanoparticles provides protein silencing in endothelial cells.* Nat Commun, 2017. 8(1): p. 191.
78. Kwon, Y. J., *Before and after endosomal escape: roles of stimuli-converting siRNA/polymer interactions in determining gene silencing efficiency.* Acc Chem Res, 2012. 45(7): p. 1077-88.
79. Gao, Y., et al., *Highly Branched Poly(beta-amino esters) for Non-Viral Gene Delivery: High Transfection Efficiency and Low Toxicity Achieved by Increasing Molecular Weight.* Biomacromolecules, 2016. 17(11): p. 3640-3647.
80. Liu, X., et al., *Structurally flexible triethanolamine-core poly(amidoamine) dendrimers as effective nanovectors to deliver RNAi-based therapeutics.* Biotechnol Adv, 2014. 32(4): p. 844-52.
81. Yang, X. Z., et al., *Sheddable ternary nanoparticles for tumor acidity-targeted siRNA delivery.* ACS Nano, 2012. 6(1): p. 771-81.
82. Kulkarni, A., et al., *Pendant polymer:amino-beta-cyclodextrin:siRNA guest:host nanoparticles as efficient vectors for gene silencing.* J Am Chem Soc, 2012. 134(18): p. 7596-9.
83. Ali, E. E., et al., *Protein Binding Characteristics of the Principal Green Tea Catechins: A QCM Study Comparing Crude Extract to Pure EGCG.* Biochem Res Int, 2019. 2019: p. 6154170.
84. Shen, W., et al., *Green Tea Catechin Dramatically Promotes RNAi Mediated by Low-Molecular-Weight Polymers.* ACS Cent Sci, 2018. 4(10): p. 1326-1333.
85. Ding, J., et al., *"Stealth and Fully-Laden" Drug Carriers: Self-Assembled Nanogels Encapsulated with Epigallocatechin Gallate and siRNA for Drug-Resistant Breast Cancer Therapy.* ACS Appl Mater Interfaces, 2018. 10(12): p. 9938-9948.
86. Zeng, H., Little, H. C., Tiambeng, T. N., Williams, G. A., & Guan, Z. (2013). Multifunctional dendronized peptide polymer platform for safe and effective siRNA delivery. Journal of the American Chemical Society, 135(13), 4962-4965.
87. Galindo-Murillo, R. and Cheatham III, T. E., 2018. Computational DNA binding studies of (−)-epigallocatechin-3-gallate. Journal of Biomolecular Structure and Dynamics, 36(13), pp. 3311-3323.
88. Kuzuhara, Takashi, et al. "DNA and RNA as new binding targets of green tea catechins." Journal of Biological Chemistry 281.25 (2006): 17446-17456.
89. Kuzuhara, Takashi, et al. "Green tea catechins inhibit the endonuclease activity of influenza A virus RNA polymerase." PLoS currents 1 (2009).
90. Chung, J. E.; et al. Self-assembled micellar nanocomplexes comprising green tea catechin derivatives and protein drugs for cancer therapy. Nat. Nanotechnol. 2014, 9 (11), 907-912.
91. Ping, Y.; et al. Supramolecular beta-Sheets Stabilized Protein Nanocarriers for Drug Delivery and Gene Transfection. ACS Nano 2017, 11 (5), 4528-4541.
92. Chen, A. M.; Zhang, M.; Wei, D. G.; Stueber, D.; Taratula, O.; Minko, T.; He, H. X. Co-Delivery of Doxorubicin and Bcl-2 siRNA by Mesoporous Silica Nanoparticles Enhances the Efficacy of Chemotherapy in Multidrug-Resistant Cancer Cells. Small 2009, 5, 2673-2677.
93. Vermeulen, Lotte M P, et al. "Endosomal size and membrane leakiness influence proton sponge-based rupture of endosomal vesicles." ACS nano 12.3 (2018): 2332-2345.
94. Leng, Qixin, et al. "Highly branched H K peptides are effective carriers of siRNA." The Journal of Gene Medicine: A cross-disciplinary journal for research on the science of gene transfer and its clinical applications 7.7 (2005): 977-986.
95. Creusat, Gaelle, and Guy Zuber. "Self-assembling polyethylenimine derivatives mediate efficient siRNA delivery in mammalian cells." Chembiochem 9.17 (2008): 2787-2789.
96. Kuzuhara, Takashi, et al. "Green tea catechins inhibit the endonuclease activity of influenza A virus RNA polymerase." PLoS currents 1 (2009).
97. Das, Sumistha, et al. "Chitosan, carbon quantum dot, and silica nanoparticle mediated dsRNA delivery for gene silencing in *Aedes aegypti*: a comparative analysis." ACS applied materials & interfaces 7.35 (2015): 19530-19535.
98. Woodrow, Kim A., et al. "Intravaginal gene silencing using biodegradable polymer nanoparticles densely loaded with small-interfering RNA." Nature materials 8.6 (2009): 526-533.
99. Lee, E. R. et al. Detailed analysis of structures and formulations of cationic lipids for efficient gene transfer to the lung. Hum. Gene Ther. 7, 1701-1717 (1996).
100. Liu, Y. et al. Factors influencing the efficiency of cationic liposome-mediated intravenous gene delivery. Nat. Biotechnol. 15, 167-173 (1997).
101. Zhang, X., J. Zhang, and K. Y. Zhu. "Chitosan/double-stranded RNA nanoparticle-mediated RNA interference to silence chitin synthase genes through larval feeding in the African malaria mosquito (*Anopheles gambiae*)." Insect molecular biology 19.5 (2010): 683-693.
102. Shukla, Jayendra Nath, et al. "Reduced stability and intracellular transport of dsRNA contribute to poor RNAi response in lepidopteran insects." RNA biology 13.7 (2016): 656-669.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:
1. A composition, comprising: a double stranded RNA (dsRNA) molecule for initiating RNA interference (RNAi) in an insect; and (−) epigallocatechin-3-O-gallate (EGCG), assembled with the dsRNA in a nanoparticle, and further comprising a polymer, wherein the ratio of polymer to EGCG is from about 1:10 to about 10:1.
2. The composition of claim 1, wherein the polymer is a polyamino acid.

3. The composition of claim 2, wherein the polyamino acid is selected from the group consisting of: polylysine, polyargenine, polyhistodine and other polyamino acids.

4. The composition of claim 1, wherein the ratio of polymer to EGCG is about 1:3.

5. The composition of claim 1, further comprising Chitosan (CS) and a cross-linker.

6. The composition of claim 5, wherein the cross-linker is sodium tripolyphosphate, dextran sulfate, or poly-D-glutamic acid.

7. The composition of claim 5, wherein the ratio of CS to cross-linker is from about 4:1 to about 6:1.

8. The composition of claim 1, further comprising protamine sulfate (PS).

9. The composition of claim 8, and further comprising a cationic-lipid formulation for transfecting insect cells.

10. The composition of claim 1, wherein the nanoparticle has a mean size equal to or less than about 200 nm.

11. The composition of claim 1, wherein the dsRNA encodes a polypeptide, or a fragment thereof, selected from the group consisting of inhibitor of apoptosis (IAP), vacuolar-sorting protein SNF7 (SNF7), snakeskin (SSK), and off-track (OTK), and combinations thereof.

12. A method of inducing RNAi in a cell, comprising: contacting the cell with the composition comprising: a double stranded RNA (dsRNA) molecule for initiating RNA interference (RNAi) in an insect; and (−) epigallocatechin-3-O-gallate (EGCG), assembled with the dsRNA in a nanoparticle, and further comprising a polymer, wherein the ratio of polymer to EGCG is from about 1:10 to about 10:1.

13. The method of claim 12, wherein the cell is in an insect.

14. The method of claim 13, wherein the insect is a mosquito.

15. The method of claim 13, wherein the insect is a coleopteran insect, an Asian longhorn beetle, or a fall armyworm.

16. The method of claim 12, wherein contacting the cell with the composition suppresses expression of one or more genes selected from the group consisting of dsIAP, dsSNF7, dsSSK, dsOTK, and combinations thereof.

* * * * *